(12) United States Patent
Karlsson-Parra et al.

(10) Patent No.: US 9,034,317 B2
(45) Date of Patent: May 19, 2015

(54) COMPOSITION FOR INHIBITING TUMOR CELL PROLIFERATION

(75) Inventors: Alex Karlsson-Parra, Uppsala (SE);
Bengt Andersson, Mölndal (SE);
AnnaCarin Wallgren, Uppsala (SE)

(73) Assignee: IMMUNICUM AB, Goeteborg (SE)

( * ) Notice: Subject to any disclaimer, the term of this patent is extended or adjusted under 35 U.S.C. 154(b) by 187 days.

(21) Appl. No.: 13/522,741

(22) PCT Filed: Feb. 10, 2011

(86) PCT No.: PCT/EP2011/051952
§ 371 (c)(1),
(2), (4) Date: Aug. 28, 2012

(87) PCT Pub. No.: WO2011/098516
PCT Pub. Date: Aug. 18, 2011

(65) Prior Publication Data
US 2012/0328662 A1    Dec. 27, 2012

Related U.S. Application Data

(60) Provisional application No. 61/303,153, filed on Feb. 10, 2010.

(30) Foreign Application Priority Data

Feb. 10, 2010 (SE) ..................................... 1050133

(51) Int. Cl.
*A01N 63/00* (2006.01)
*C12N 5/071* (2010.01)
*C12N 5/0784* (2010.01)

(52) U.S. Cl.
CPC .................................. *C12N 5/0639* (2013.01)

(58) Field of Classification Search
None
See application file for complete search history.

(56) References Cited

U.S. PATENT DOCUMENTS

| 8,728,806 | B2* | 5/2014 | Decker et al. | 435/325 |
| 2004/0214783 | A1* | 10/2004 | Terman | 514/33 |
| 2009/0123441 | A1 | 5/2009 | Braughler et al. | |

FOREIGN PATENT DOCUMENTS

| WO | WO 2007/110240 | 10/2007 | C12N 5/06 |
| WO | WO 2008/110569 | 9/2008 | G01N 33/50 |

OTHER PUBLICATIONS

Fujita et al., Feb. 3, 2009, Canc. Res. vol. 69: 1587-1595.*
Ahonen et al., 1999, Cell. Immunol. vol. 197: 62-72.*
Lebre et al., 2005, Imm. Cell. Biol. vol. 83: 525-535.*
Gautier et al., 2005, J. Exp. Med. vol. 201: 1435-46.*
Blanco et al., 2008, Cytokine and Growth Factor Reviews: 19: 41-52.*
Alder, J., et al. (2006) "Interferon-γ dose-dependently inhibits prostaglandin $E_2$-mediated dendritic-cell-migration towards secondary lymphoid organ chemokines" Vaccine, Elsevier Ltd, vol. 24, No. 49-50, pp. 7087-7094.
Boullart, A., et al. (2008) "Maturation of monocyte-derived dendritic cells with toll-like receptor 3 and ⅞ ligands combined with prostaglandin $E_2$ results in high interleukin-12 production and cell migration" Cancer Immunology Immunother, vol. 57, No. 11, pp. 1589-1597.
Gustafsson, K., et al. (2008) "Recruitment and activation of natural killer cells in vitro by a human dendritic cell vaccine" Cancer Research, American Association for Cancer Research, vol. 68, No. 14, pp. 5965-5971.
International Search Report for PCT/EP2011/051952 dated May 5, 2011.
Grauer, O., et al. (2007), "Toll-like receptor triggered dendritic cell maturation and IL-12 secretion are necessary to overcome T-cell inhibition by glioma-associated TGF-β2", *J. Neurooncol*, 82: 151-161.

* cited by examiner

*Primary Examiner* — Amy Juedes
(74) *Attorney, Agent, or Firm* — Harness, Dickey & Pierce, P.L.C.

(57) ABSTRACT

This invention pertains to cancer immunotherapy, by providing a proinflammatory dendritic cell (DC), which has been stimulated to maturation ex vivo by specific treatment, a method for such treatment and a composition comprising the proinflammatory DC. The DC may be used as a cell based immunotherapy for inhibiting tumor cell proliferation.

20 Claims, 14 Drawing Sheets

US 9,034,317 B2

COMPOSITION FOR INHIBITING TUMOR CELL PROLIFERATION

Priority Statement

This application is a national phase under 35 U.S.C. § 371 of PCT International Application No. PCT/EP2011/051952 which has an International filing date of 10 Feb. 2011, which claims priority under 35 U.S.C. § 119 to U.S. Provisional Application No. 61/303,153, filed 10 Feb. 2010 and Swedish Patent Application No. 1050133-6 filed on 10 Feb. 2010. The contents of each application recited above are incorporated herein by reference in their entirety.

FIELD OF THE INVENTION

This invention pertains in general to the field of cancer therapy. More particularly the invention relates to cancer immunotherapy, and more particularly to a cell based immunotherapy for inhibiting tumor cell proliferation.

BACKGROUND

Vaccines have long been used for the prevention of infectious diseases, such as viral or microbial infections. The cell-mediated arm of the immune system is extensively involved in providing the host with the ability to defend, recover from infections and to prevent further infections by the same antigen. Cell-mediated immune mechanisms are also thought to be useful against cancer.

Dendritic cells (DCs), the most potent antigen-presenting cells (APC), play a central role in the initiation and regulation of immune responses. They have the unique ability to prime naive T cells and to elicit and induce effective cytotoxic T lymphocyte (CTL) responses. DC precursors are present in the circulating blood and can quickly be recruited to sites of infection or inflammation. When DC precursors differentiate into immature DCs they become very effective in taking up and processing exogenous protein antigens. In response to various maturation stimuli, such as bacterial and viral components expressing Toll-like receptor (TLR) ligands, inflammatory cytokines and/or specific T cell interactions (CD40/CD40-ligand interactions), they initiate a differentiation process leading to decreased antigen uptake and processing capacities and enhanced expression of co-stimulatory and MHC molecules. Importantly, signal strength and persistence of the signals induced by direct pathogen recognition (eg, TLRs) or CD40 ligation has been shown to be critical determinants of specific DC functions. DCs are therefore terminally induced by activation-factors at peripheral sites, to fulfill 1 of 2 mutually exclusive functions—that is, either to migrate to lymph nodes (as mature migratory DCs) for efficient T-cell interaction, or to condition the microenvironment by producing large quantities of inflammatory mediators including chemokines and cytokines (as mature proinflammatory DCs).

Existing cancer immunotherapy strategies that focus on DCs are all based on the premise that the quality of the T cell response depends mainly on the ability of migratory DCs to process and present tumor antigens to T cells in secondary lymphoid organs and thus create a tumor-specific CTL response, which leads to an immunological attack on the cancer cells. Data from different mouse tumor models have shown that such response can been trigged according to one out of three main strategies, well known to a person skilled in the art. These immunotherapeutic anticancer strategies are now actively tested in humans but all with limited success.

The first strategy is to activate and mature antigen-loaded migratory DCs from the tumor-bearing patient ex vivo and subsequently reintroduce them to the same patient. Antigen-loading is typically performed by adding tumor associated antigens (lysed tumor cells, protein, peptides or nucleic acids coding for such antigens) to monocyte-derived immature DCs followed by activation/maturation of antigen-loaded DCs with different combinations of inflammatory factors. The reintroduced DCs are supposed to migrate to draining lymph nodes where they prime tumor-specific T lymphocytes. DC-primed T lymphocytes, particularly CTLs, then travel to the tumor site where they subsequently induce tumor-cell apoptosis.

In the clinical setting, ex vivo manipulation of patients own, i.e. autologous, DCs is however time consuming and exposes the patient to increased risk of infection. Also, the manipulation process in which the DCs are pulsed with tumor antigens and activated to migratory DCs that efficiently present tumor antigens is tedious.

The second main strategy, which circumvents the need for ex vivo propagation of patient-derived migratory DCs, comprises administration of tumor antigens, including irradiated allogeneic tumor cells, or plasmids coding for tumor antigens, into intact normal tissues, including subcutaneous or intramuscular injections. The tumor antigens are supplemented with so called adjuvants, which are aimed to trigger a DC-mediated immune response in vivo. Most commonly, chemokines, cytokines or plasmids coding for these factors, and/or DC-maturating factors such as tumor necrosis factor α (TNF-α), and/or TLR agonists are used as adjuvants.

However, administration of exogenous tumor antigen is a tedious process.

The third main strategy, which also circumvents the need for ex vivo propagation of patient-derived migratory DCs, included in the first main strategy, and additionally circumvents the need of exogenous tumor antigen, included in the second main strategy, regards an adjuvant which is injected directly into tumors. Thus, the adjuvant is aimed at targeting DCs in vivo and the tumor of the patient acts as a source for tumor associated antigens. Adjuvants that have been tested are similar to those described in the second main strategy: chemokines, cytokines or plasmids coding for these factors, and/or DC-maturating factors such as TNF-α, and TLR agonists. However, a viable tumor may be a poor source of tumor associated antigen for recruited immature DCs, due to insufficient numbers of dying, preferably induced by apoptosis, tumor cells that can be engulfed by these DCs.

All the abovementioned three strategies have been tested in human cancer patients, but with limited success. Hence, there is an obvious need for more efficient therapeutic vaccines and improved methods of treatment of cancer.

SUMMARY

Accordingly, the present invention preferably seeks to overcome the above-identified deficiencies in the art singly or in any combination and solves at least the above mentioned problems by providing a proinflammatory mature dendritic cell that produce high levels of desirable chemokines and interleukin 12 (IL-12), a composition comprising such proinflammatory dendritic cell, a method for producing such proinflammatory dendritic cell, a use of said proinflammatory dendritic cell or said composition as a medicament and a use of said dendritic cell or said composition to treat cancer.

Thus, in a first aspect, a proinflammatory dendritic cell (DC), which has been stimulated to maturation ex vivo by treatment with the substances polyinosinic-polycytidylic acid sodium salt (poly-I:C), resiquimod (R848) and interferon gamma (IFN-γ) is provided.

In a second aspect, a composition comprising proinflammatory DC according to the first aspect and peripheral blood mononuclear cells (PBMCs) is provided.

In a third aspect, a method for producing proinflammatory DC according the first aspect is provided. Said method comprises the steps of providing peripheral blood mononuclear cells (PBMCs), isolating monocytes from said PBMCs, generate immature DCs (iDCs) from said monocytes, and induce maturation of the iDCs by adding poly-I:C, R848 and IFN-γ to the iDCs to obtain proinflammatory DC.

In a fourth aspect, a method for producing a composition according to the second aspect is provided. Said method comprises the steps of providing peripheral blood mononuclear cells (PBMCs), obtaining proinflammatory mature DC according to the first aspect, and mixing said PBMCs and said proinflammatory mature DC.

In a fifth aspect, a proinflammatory DC according to the first aspect or a composition according to the second aspect, for use as a medicament is provided.

In a sixth aspect, a proinflammatory DC according to the first aspect or a composition according to the second aspect, for use as a medicament in an individual other than the source of the proinflammatory mature DC or the PBMCs is provided.

In a seventh aspect, a proinflammatory DC according to the first aspect, or a composition according to the second aspect, for use in treatment of cancer.

In an eight aspect, proinflammatory DC according to the first aspect, or a composition according to the second aspect, for use in treatment of cancer in an individual other than the source of the proinflammatory mature DC or the PBMCs is provided.

Further embodiments of the invention are defined in the dependent claims.

The present invention differs from the prior art in that it produces high levels of desirable cytokines, such as chemokine (C-X-C motif) ligand 9 (CXCL9), also known as MIG, C-C motif chemokine 3 (CCL3), also known as macrophage inflammatory protein 1-alpha (MIP-1α), tumor necrosis factor alpha (TNF-α), IL-1β, and IL-12 after withdrawal of activation stimuli, and are thus suitable for use, such as injection, without presence of exogenous maturing stimulatory factors.

When injected intratumorally into a patient in an allogeneic fashion, i.e. the patient is different from a donor from whom the proinflammatory DC, or the PBMCs used to create the proinflammatory DC originate, such proinflammatory DC will activate the patients own DCs so that they develop into tumor-loaded migratory DCs. This effect is due to the ability of injected proinflammatory DC to produce large amounts of a combination of desirable cytokines and IL-12, including the DC, NK cell and memory T cell recruiting chemokine MIP-1 alpha/CCL3, the NK cell and memory T cell recruiting chemokine MIG/CXCL9, as well as the NK activating cytokine IL-12. Moreover, an advantage with mature DCs, such as proinflammatory mature DC, over immature DCs, can potentiate NK cell activation by cell-cell contact. The fact that the proinflammatory DC are free from strong exogenous activating, such as maturing, factors is an advantage, since the presence of strong exogenous activating factors within the tumor may otherwise trigger a differentiation of the patients own intratumorally recruited DCs into patient specific, i.e. own, proinflammatory DCs and not into desirable patient specific migratory DCs. Thus, at least 18 hours of stimulation will probably be needed to achieve a high expression of molecules like CD86 on a maturing DC, in order to give it optimal ability to activate an NK cell. According to prior art, activated/mature DC are incapable of producing significant amounts of IL-12 after 18 hours. If aborting activation after only 8 hours, a production is remaining. However, these DC have not had time to upregulate relevant NK activating molecules.

Transplantation with allogeneic organs, tissues or mature DCs is further known to induce a strong immunization leading to expansion of alloreactive CD4+ T cells that are specific for allogeneic MHC-derived peptides presented on self-MHC class II molecules (called the indirect pathway of allorecognition). By using allogeneic proinflammatory DC as for intratumoral injection, the DC will subsequently be killed (rejected) by the host immune system and thereby become a source of highly immunogenic CD4+ T helper cell epitopes (allogeneic MHC-derived peptides) that will be captured by recruited own DCs and most likely will contribute to break CD8 tolerance to tumor antigens in tumor-bearing patients. The proinflammatory DC would thus act as adjuvant and not as migratory DCs, which is both advantageous and different compared to prior art. For example, if prostaglandin E2 (PGE2) is included in different DC maturation cocktails, the mature DC will become a migratory DC that rapidly will leave the injection site (tumor), which is disadvantageous within the context of this invention.

By using allogeneic DC, i.e. in an individual other than the source, or donor, of the proinflammatory mature DC or the PBMCs, such potential adjuvant does not have to be individually prepared for each specific patient and allows for large scale production with subsequent lower manufacturing costs. In addition, the vaccine can be frozen and shipped across great distances, which further enhances its commercial viability.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Figure 1:
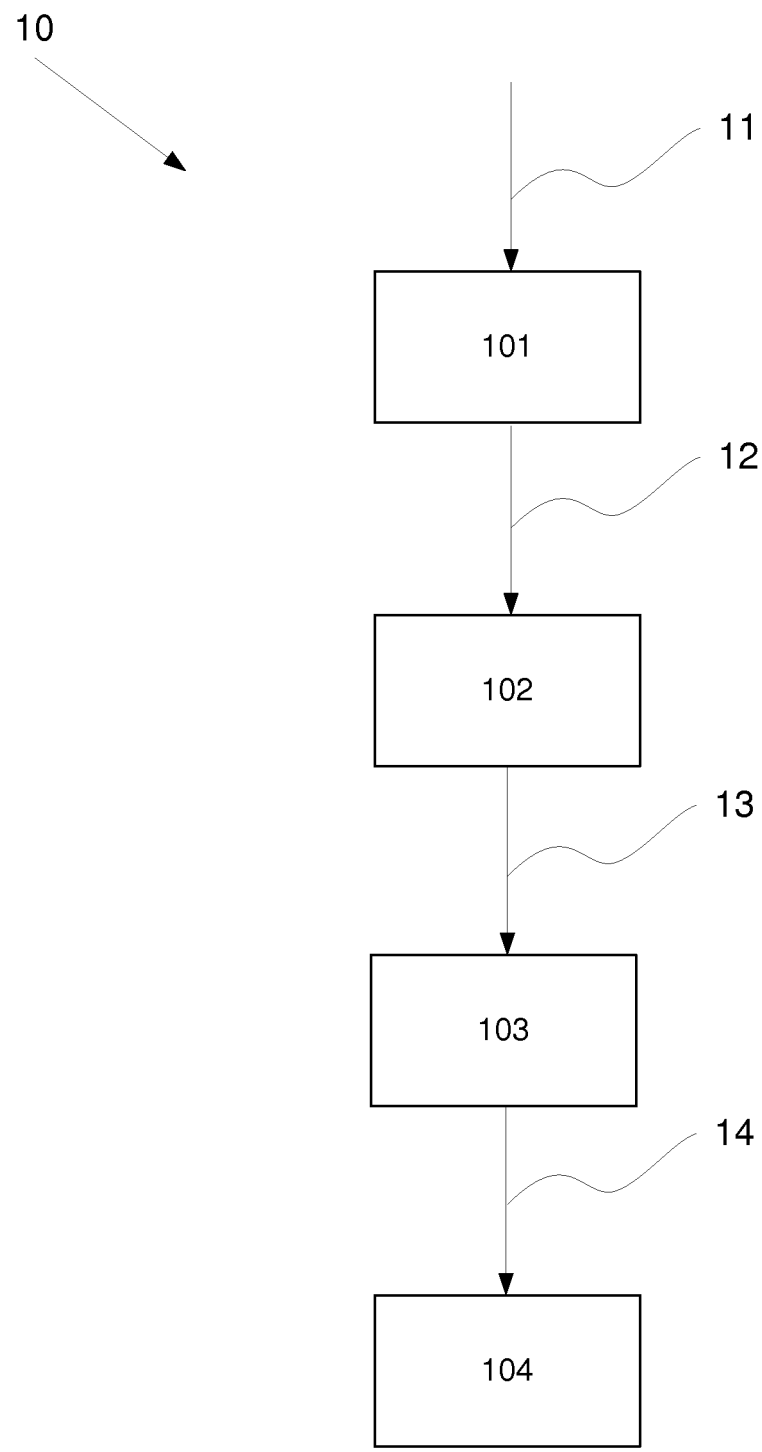
FIG. 1 is a schematic illustration of a method according to the third aspect.

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Intratumorally injected adjuvants that are aimed at inducing an efficient antitumoral immune response most likely have to induce 3 events within the injected tumor, all important to achieve CTL mediated tumor eradication.

Firstly, immature DC (iDC) needs to be recruited to the tumor, in order to be exposed to the tumor antigen. It is well established within the art that the chemokine MIP-1α/CCL3 has a strong ability to stimulate recruitment of iDC, including intratumoral recruitment of iDC in vivo.

Secondly, it is important to induce apoptosis of tumor cells in order to make the tumor antigens available to the recruited iDC. Several different methods for achieving this exist within the art, including methods that trigger intratumoral recruitment and activation of natural killer (NK) cells. NK-cell mediated primary killing of susceptible tumor cells, mainly due to induction of apoptosis, in different mouse models has repeatedly been shown to efficiently evoke a subsequent DC-mediated development of tumor-specific cytotoxic T cell responses to the parental, NK cell resistant, tumor cells. NK cells are known to express the chemokine receptor CXCR3, and CXCR3-dependent recruitment of NK cells has been demonstrated in several animal models. One well-known CXCR3-ligand is MIG/CXCL9 and there is evidence that NK cells accumulate after intratumoral injection of MIG/CXCL9.

In order for the recruited NK cells to effectively kill tumor cells, the presence of NK-cell activating factors such as IL-12, a potent activator of the NK cell killing activity in vitro and in vivo, is most likely also necessary.

Thirdly, the maturation of recruited iDC into mature migratory DC must be induced.

Early stages of viral infections (normally leading to Th1-deviated immune responses) are usually associated with local recruitment and activation of both DCs and NK cells. In a recent study, human peripheral blood NK cells that had been exposed to either IL-12 or IL-4 during short (overnight) incubation were investigated as to ability to induce maturation of DC. Notably, only NK cells that had been stimulated with IL-12 were able to induce substantial DC maturation. It was therefore concluded that NK cells exposed to IL-12 for a time interval compatible with in vivo responses may favor the selection of appropriate mature DCs for subsequent Th1 cell priming in secondary lymphoid organs (5). These human in vitro data are in line with in vivo data from mouse models showing that Th1 responses become significantly increased when injection of antigen-loaded DC in mice is followed by an accumulated recruitment of NK-cells, compared to situations in which no NK recruitment was observed.

Maturation of Th1-polarizing DC has also been shown to be induced by soluble factors produced by polyclonally activated T cells. Treatment of immature DC with a T cell conditioned medium (TCCM) prepared from cell-free supernatants of anti-CD3-activated T cells, or T cells activated by dual stimulation with anti-CD3 and anti-CD28 has been shown to contain several soluble factors including CD40-ligand, TNF-α, and IFN-γ. In contrast to moderate up-regulation of co stimulatory molecules by the addition of individual cytokines or monocyte-conditioned medium, treatment of immature DC with TCCM has been shown to induce a marked increase in the expression of co stimulatory molecules in a dose-dependent manner. The ability of TCCM to induce such phenotypic changes is further abrogated by neutralizing antibodies specific for CD40L, TNF-α and IFN-γ indicating that these factors present in TCCM are mainly implicated in the maturation of DC. Importantly, TCCM-treated DC can produce high levels of Th1-deviating IL-12.

Finally, it is known that CD4+ T cells play crucial roles in priming, expansion, and memory and in survival of CD8+ CTLs by "helping" migratory DCs during their cognate interaction with antigen-specific CD8+ T cells in draining lymph nodes. A number of studies within the area of cancer immunotherapy have relied on the approach that CD4+ T cell recognition of MHC class II peptides from the wild-type tumor Antigen would provide the help needed for CTL induction. However, help provided by peptides from the tumor antigens will often be weak or absent due to tolerance induction of CD4+ T cells toward these self-proteins that evolves during tumor progression, which could hamper the therapeutic effect of a vaccine. Recent findings demonstrate that addition of a non-self CD4+ T helper epitopes to tumor associated self-proteins at the vaccination site is sufficient to break established CD8 tolerance to tumor associated antigens in mouse models.

Taken together, all these data indicate that an intratumorally injected adjuvant that is aimed at inducing an efficient antitumoral adaptive (T cell mediated) immune response should be characterized by a high and sustained production of MIP-1α/MIP-1α/CCL3 (DC, NK and memory T cell recruitment), MIG/CXCL9 (NK cell and memory T cell recruitment), IL-12p70 (NK cell mediated release of tumor antigens and NK cell-mediated maturation of migratory DCs) and finally, the presence of immunogenic non-self proteins that may act as CD4+ T cell helper epitopes during DC-mediated priming of tumor-specific CD8+ T cells in the draining lymph node.

Human monocyte-derived DCs have the potential to produce high levels of MIP-1α/CCL3, IL-12p70 and MIG/CXCL9 during persistent stimulation with certain TLR-ligands that also lead to their maturation. In order to inject such persistently activated proinflammatory mature DCs intratumorally, they have to be washed prior to intratumoral installation. If not, the concurrent administration of stimulating agents (aimed to induce proinflammatory DCs ex vivo) most likely will lead to a strong and persistent activation also of intratumorally recruited immature DCs, leading to their differentiation into proinflammatory mature DCs instead of the desired differentiation into migratory mature DCs. Unfortunately, cessation of maturating stimuli like TLR4 ligands or CD40L at time points when the DCs have differentiated into mature DCs (usually after more than 12 hours of stimulation) is known to induce a rapid down-regulation of inflammatory cytokine production, including IL-12 production. Activation methods must therefore be used that activate DCs into proinflammatory mature DC with sustained production of desirable factors after cessation of the activation-inducing factors.

The present inventors found a method for producing a proinflammatory mature DC, which after withdrawal of persistent stimulation with strong activating factors, thus making the DCs free from stimulation factors, which produce surprisingly high levels of desirable chemokines and IL-12. The proinflammatory mature DCs may be administered to a patient in an allogeneic fashion, i.e. to a patient other than the source of the DC.

The proinflammatory mature DCs may be mixed with peripheral blood mononuclear cells (PBMCs), thus forming a composition. The proinflammatory mature DCs may be coated with superantigen, such as *Staphylococcus aureus* Enterotoxin B (SEB), which will cause a polyclonal activation of T cells within the PBMC population.

When administered to a patient, the proinflammatory mature DCs or the compositions will induce an immune response that will lead to a cellular immune response against the tumor that kills the tumor.

The effect is extra strong if the patient is not the donor of the PBMCs either as such or as the source of the proinflammatory mature DCs, i.e. they are allogeneic to the patient. Then, the proinflammatory mature DCs or the composition will act as non-self CD4+ T helper epitopes.

The proinflammatory mature DCs or the composition will contribute to attract patients own DC, NK cells and T cells to the site of injection, by the ability of proinflammatory mature DCs to produce high levels of relevant chemokines, such as MIP-1α/CCL3, and to activate recruited NK cells, by cell-cell dependent interations and the ability of proinflammatory mature DCs to produce high levels of the cytokine IL-12, that will lead to antigen-loading of patients own recruited DCs with immunogenic tumor material from NK cell-killed tumor cells.

Preferably, the composition 100 is injected directly into the tumor. The ability to attract DCs into and throughout the tumors is important, since in most studied cancer patients, DCs have been found mainly at the periphery of the tumors, which may limit their interaction with tumors cells. Importantly, the capacity of chemokines to recruit patients own circulating DCs to the tumor site exposes tumor cells to freshly generated/recruited DCs (as opposed to local DCs), which may be less affected by an immunosuppressive tumor milieu.

In an embodiment according to FIG. 1, a method 10 is provided wherein peripheral blood mononuclear cells (PBMCs) 101 are provided 11. Monocytes 102 are isolated 12 from said PBMCs 101. Immature DCs (iDCs) 103 are generated 13 from said monocytes 102 and maturation of the iDCs 103 is induced 14 by adding the activation-inducers poly-I:C, R848 and IFN-γ to the iDCs 103, followed by washing to remove all activating factors thus resulting in stimulation factor free, proinflammatory mature DC 104.

In an embodiment, the induction 14 of maturation of the iDCs 103 further comprise adding at least one of the substances chosen from the group consisting of: IFN-α, IL-1β and TNF-α.

In an embodiment, the generation 13 of iDCs is induced by culturing monocytes in an aqueous media comprising IL-4 and GM-CSF for 2 to 7 days, such as 3 to 5 days, or 3 or 5 days.

Figure 2A:
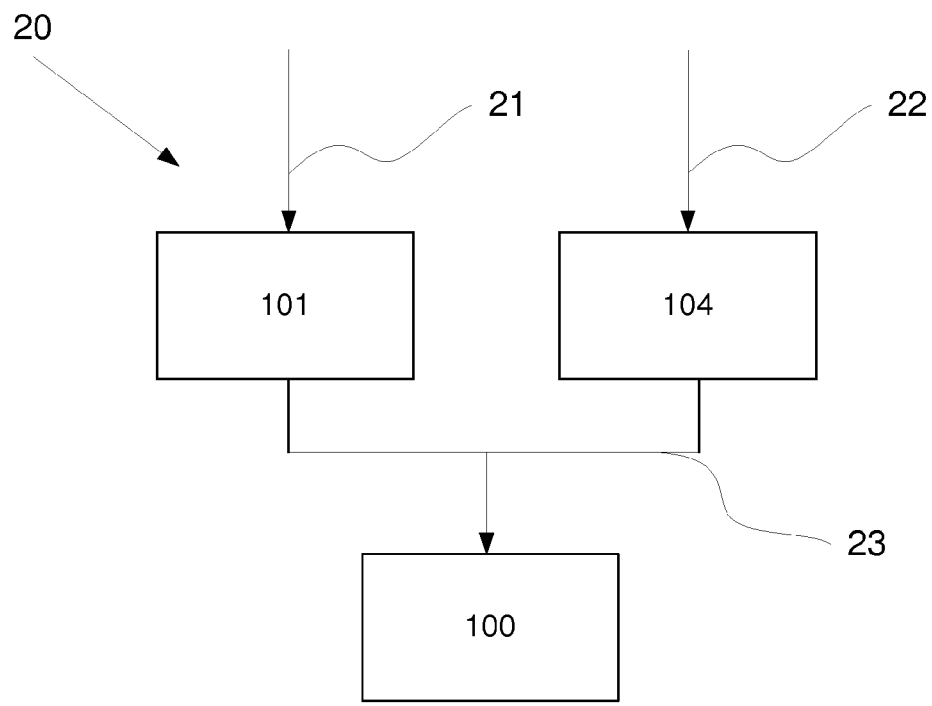
FIG. 2 is a schematic illustration of a method according to the fourth aspect.

In an embodiment according to FIG. 2A, a method 20 for producing a composition 100, such as co-culture of proinflammatory DCs 104 and PBMCs 101 is provided. The method comprises providing 21 peripheral blood mononuclear cells (PBMCs) 101, obtaining 22 proinflammatory mature DCs 104, and mixing 23 said PBMCs 101 and said proinflammatory mature DCs 104.

Figure 2B:
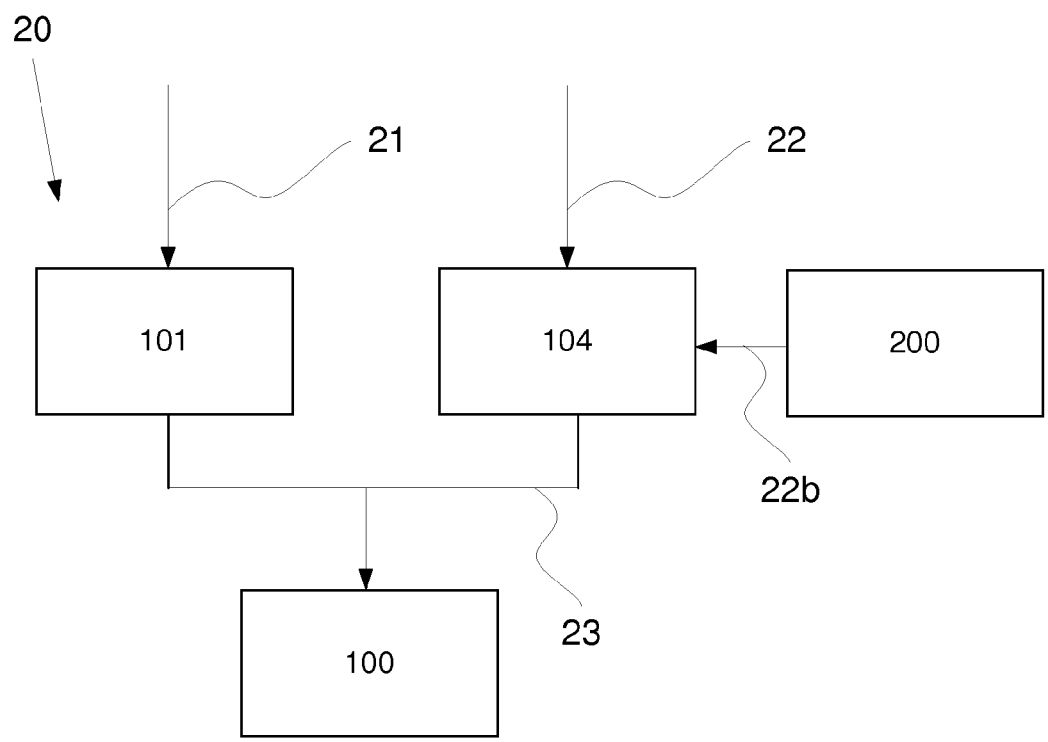

In an embodiment according to FIG. 2B, the method 20 for producing a composition 100 further comprising the step, before the mixing, of treating 22b the proinflammatory mature DC 104 with a superantigen 200.

The above embodiments will be described in further detail below.

Experimental

The following experimental embodiment is not intended to be limited to the specific form set forth herein. Rather, the invention is limited only by the accompanying claims and other embodiments than the specific abovementioned embodiments are equally possible within the scope of the appended claims.

Isolation of PBMC and Monocytes

Peripheral blood mononuclear cells (PBMCs) 101 were separated from peripheral blood obtained from healthy donors (Sahlgrenska sjukhuset, Göteborg, Sweden) by density gradient centrifugation using Lymphoprep (Nycomed, Pharma, Oslo, Norway), well known to a person skilled in the art. PBMCs 101 were resuspended in Cellgro medium (Cell Genix, Freiburg, Germany) to a final concentration of 2.5× $10^6$/mL followed by incubation in a flat-bottomed 24-well plate (1 ml/well) in 37° C., 6% $CO_2$. After 2 h the nonadherent cells were removed, while the remaining adherent cells were washed twice with PBS, resulting in isolated monocytes 102 (mainly consisting of CD14+ cells).

Generation of DCs

In order to differentiate the monocytes 102 into immature DCs 103, the monocytes 102 from the isolation step were cultured in fresh aqueous medium, such as Cellgro medium, supplemented with inducers, i.e. 1000 U/mL recombinant human IL-4 and 1000 U/mL recombinant human GM-CSF (all from CellGenix, Freiburg, Germany) in either 3 or 5 days.

Generation of monocyte-derived immature DCs (iDCs) 103 in IL-4 and GM-CSF is a well-accepted in vitro model, and the cells may be considered analogous to peripheral tissue DCs.

Maturation of DCs

Following 3 or 5 days of culture in Cellgro medium supplemented with IL-4 and GM-CSF, the maturation of the immature DCs 103 was induced adding either 20 μg/mL polyI:C (Sigma, Steinheim, Germany), an immunostimulant specific to the TLR-3 receptor also known as polyinosinic:polycytidylic acid or polyinosinic-polycytidylicf acid sodium salt, and 2.5 μg/mL R848 (Sigma, Steinheim, Germany), toll-like receptor 7/8-ligand also known as resiquimod, to the culture media, or the combination polyI:C and R848 supplemented with 1000 U/ml interferon gamma (IFN-γ, R&D systems, Minneapolis, USA). After 18 h of incubation, the cells were washed three times and further incubated in fresh medium (without addition of exogenous activating factors) for 24 h to obtain proinflammatory mature DC 104 according to an aspect.

Culture supernatants from the cultures were harvested according to protocols well known to a person skilled in the art.

An ELISA analysis was performed on the supernatants as described below, in order to analysis the levels of the chemokines CCL3/MIP-1α, CCL5/RANTES, CXCL9/MIG, CCL2/Monocyte chemotactic protein-1 (MCP-1), and the cytokine interleukin 12 (IL-12).

Co Culture of DC and PBMCs

PBMCs 101 were obtained according to above and proinflammatory mature DC 104 were also obtained according to above.

In order to achieve a rapid maturation and polyclonal activation of T-cells from the PBMCs 101, 0.01 μg/ml SEB (R&D systems, Minneapolis, USA) was added to the DC culture in the maturation step, 30 min before washing. After washing in PBS three times the proinflammatory mature DC 104 (2.5× $10^5$ cells/mL) were co-cultured with 1×$10^6$ cells/mL allogeneic PBMCs (isolated from peripheral blood of healthy donors as described above), in a total volume of 1 mL for 24 h.

The culture supernatants from the co culture of proinflammatory mature DC 104 and allogeneic PBMCs, so called MLR supernatants, were harvested and subsequently stored at −80° C. The supernatants were later analyzed for the presence of the well-known DC-activating/maturating factors IFN-γ, TNF-α and IL-1β by ELISA as described below. The supernatants were also studied as to induction of phenotypic maturation of iDCs, also described below.

ELISA

CCL3/MIP-1α, CCL5/RANTES, CXCL9/MIG, CCL2/MCP-1, IL-12, TNF-α, IL-1β and IFN-γ levels were measured by enzyme-linked immune adsorbent assay (ELISA) using Duo Set ELISA Development System from R&D systems, Minneapolis, USA according to the manufacturers instructions.

Phenotypic Maturation Examination

Monocyte-derived dendritic cells 103 (iDCs) were generated as described above. After 5 days of incubation in Cellgro supplemented with IL-4 and GM-CSF, the immature DCs 103 were incubated at 37° C. for 24 h in 300 μl of the above stated MLR supernatants and 100 μl fresh Cellgro medium. DCs cultivated without the addition of supernatants were used as control. To determine whether the MLR supernatants are inducing maturation, the samples were stained with PE anti-human CD86 in combination with FITC anti-human CD83. Mouse IgG1 and IgG2 stained with FITC and PE were used as isotype controls (all from BD Biosciences, California, USA). The samples were analyzed by flow cytometry (FACS) using Cell Quest software (BD Bioscience, California, USA).

Results

Below, the results from the experimental part are commented.

Sustained Production of Desirable Inflammatory Chemokines

Figure 3A:
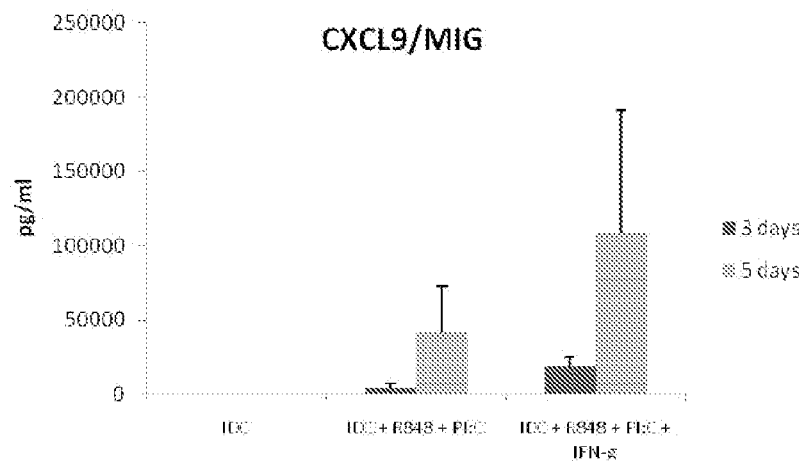
FIG. 3 are graphs showing production of CCL3/MIP-1α (FIG. 3C), CCL5/RANTES (FIG. 3A) and CXCL9/MIG (FIG. 3B) by proinflammatory mature DC according to the first aspect.
Figure 3B:
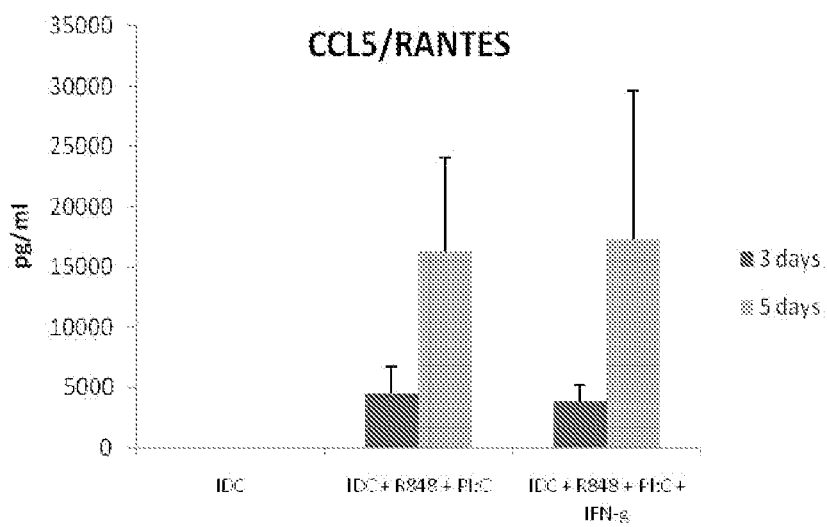
Figure 3C:
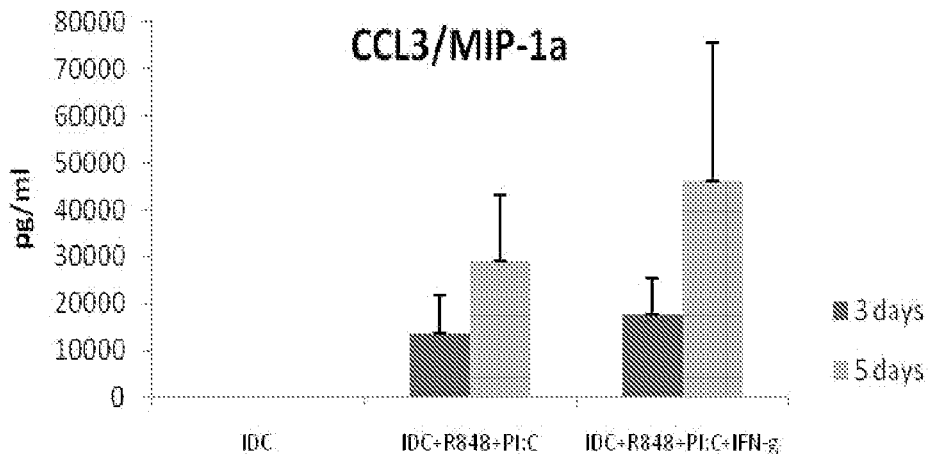

As shown in FIG. 3, the production of CCL3/MIP-1α (FIG. 3C), CCL5/RANTES (FIG. 3A) and CXCL9/MIG (FIG. 3B) by proinflammatory mature DC 104 from 3 investigated blood donors was higher if the iDCs had been induced by culturing for 5 days in GM-CSF and IL-4 before combined TLR stimulation, i.e. induction 14 of maturation, as compared to culture for 3 days in GM-CSF and IL-4. Moreover, combined TLR stimulation with addition of IFN-γ gave the highest levels of CCL3/MIP-1α and CXCL9/MIG, while production of CCL5/RANTES was unaffected by the addition of IFN-γ.

Thus, a proinflammatory dendritic cell (DC), which has been stimulated to maturation ex vivo by treatment with the substances polyinosinic-polycytidylic acid sodium salt (poly-I:C), resiquimod (R848) and interferon gamma (IFN-γ).

In an embodiment, proinflammatory dendritic cell (DC) has in addition been stimulated with at least one of the substances chosen from the group consisting of interferon α (IFN-α), interleukin 1, beta (IL-1β) and tumor necrosis factor α (TNF-α).

Notably, the recorded high levels of relevant chemokines were produced after withdrawal of maturation stimuli. The fact that the proinflammatory mature DC 104 are free from strong exogenous activating, such as maturing, factors is an advantage, since the presence of strong exogenous activating factors within the tumor may otherwise trigger a differentiation of the patients own intratumorally recruited DCs into patient specific, i.e. own, proinflammatory DCs and not into desirable patient specific migratory DCs.

The proinflammatory mature DC produces at least 25 000 pg IL-12/mL/$10^6$ cells, such as 120 000 pg/mL/$10^6$ cells, at least 100 000 pg CXCL9/mL/$10^6$ cells, such as 400 000 pg/mL/$10^6$ cells, and at least 40 000 pg CCL3/mL/$10^6$ cells, such as 180 000 pg/mL/$10^6$ cells, during 24 h after withdrawal of stimuli.

The proinflammatory mature DC may also produce CCL5/RANTES, such as 17500 pg/mL/$10^6$ cells, during 24 h after withdrawal of stimuli.

No detectable levels (detection level 312 pg/mL) of CCL2/MCP-1 where found (data not shown). FIG. 3 shows levels of CCL3/MIP-1 alpha (FIG. 3C), CCL5/RANTES (FIG. 3A) and CXCL9/MIG (FIG. 3B), as obtained by ELISA analysis. Results shown are mean values±SD from three individuals. The respective Y-axis show the amount of the respective substance produced in pg/mL/2.5×$10^5$ cells, during 24 h after withdrawal of stimuli. The X-axis show the different combinations measured.

Sustained Production of IL-12p70

Figure 4:
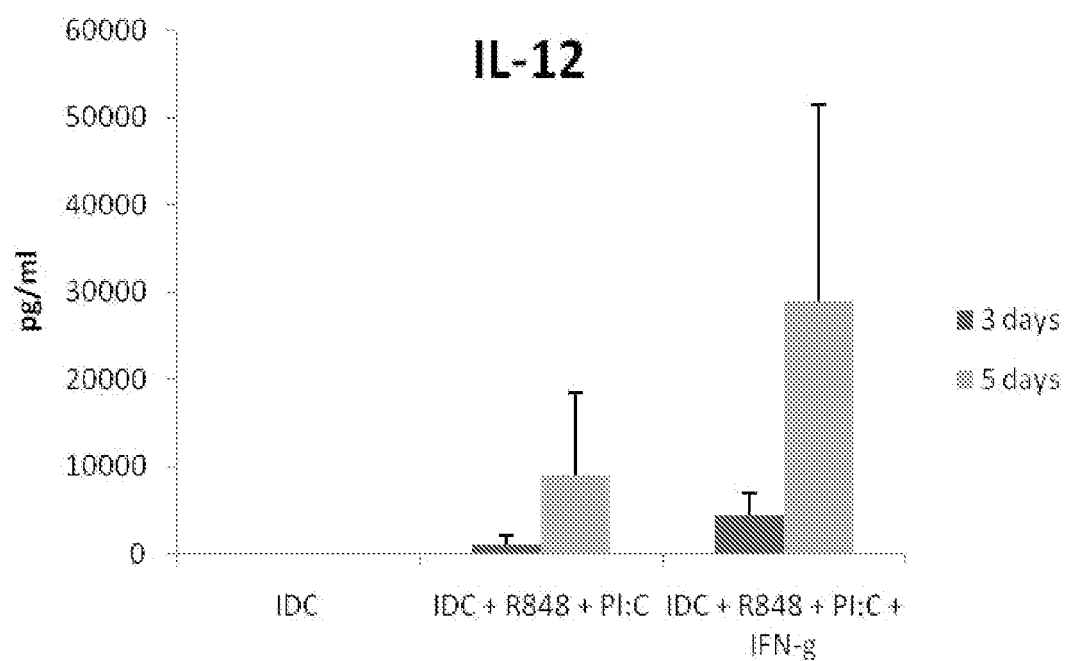
FIG. 4 is a graph showing production of IL-12 by proinflammatory mature DC according to the first aspect.

Since combined TLR stimulation, i.e. induction 14 of maturation, with or without concurrent stimulation with IFN-γ was found to induce a sustained and strong production of NK cell-recruiting chemokines (CCL3/MIP-1α, CCL5/RANTES and CXCL9/MIG) in proinflammatory mature DC 104, it was of interest to investigate if such DCs concurrently could release IL-12, such as IL-12p70, a well-known NK-cell activating factor. As shown in FIG. 4, dual stimulation of TLRs (such as R848 and PolyI:C) were shown to induce a strong and sustained production of IL-12p70 after withdrawal of maturation stimuli, such as the activation-inducers. Moreover, addition of IFN-γ during activation further enhanced the production of IL-12p70. Similar to the production of chemokines, IL-12p70 production was optimal (in 3 out of 4 experiments) when monocytes were cultured in GM-CSF and IL-4 for 5 days, as compared to 3 days, before activation. FIG. 4 shows Production of IL-12p70 following induction of DC maturation. Presented data is an average±SD from three experiments with different donors. The Y-axis show the amount of the substance produced in pg/mL/2.5×$10^5$ cells, during 24 h after withdrawal of stimuli. The X-axis show the different combinations measured.

Co Culture of Mature DCs or SEB-Coated Mature DCs with Allogeneic PBMCs Induce Production of DC-Maturating Factors Proinflammatory soluble factors produced by activated NK cells and T cells are known to promote maturation of bystander immature DCs. It was therefore of interest to examine if the proinflammatory mature DC 104, when co cultured with allogeneic PBMCs (mimicking recruited immune cells) in a composition 100, were able to induce production of cytokines known to be important for maturation of DCs. In order to optimize DC-induced T cell activation, the DCs were coated with the superantigen *Staphylococcal enterotoxin* B (SEB) by adding SEB to the DC-culture at the end (30 minutes before washing) of the stimulation period with dual TLR agonists and IFN-γ. Superantigens, including SEB, are known to form complexes with MHC class II on APCs and to stimulate the T cells via the T cell receptor. A rapid polyclonal activation and both of CD4+ and CD8+ T cell occurs in response to SEB leading to an increased production of proinflammatory mediators, including TNF-α, IL-1 and IFN-γ. As much as 20% of the T cell repertoire can be stimulated by SEB, and the "hyperactivation" of T cells commonly occurs within 48 h following SEB exposure.

After repeated washings, proinflammatory mature DC 104, with or without concurrent "coating" with SEB, were co cultured with allogeneic PBMCs for 24 h and the levels of TNF-α, IL-1β and IFN-γ released in the supernatant were measured by ELISA. Other types of superantigens, such as *Staphylococcal* enterotoxin A, C, D E F, G, H and J, and *Staphylococcal* toxic shock syndrome toxin-1 (TSST-1) may also be used. As shown if FIG. 5A, co culture of SEB-coated proinflammatory mature DC 104 (stimulated with combined TLR ligands), but not immature DCs, induced a substantial production of IL-1β after co culture with allogeneic PBMCs. Co culture of SEB-coated immature DCs with allogeneic PBMCs induced a substantial production of TNF-α that was marginally enhanced by using mature DCs. Production of IL-1β or TNF-α was not substantially affected by adding IFN-γ to dual TLR stimulation during DC maturation. Notably, SEB-coating markedly contributed to the release of IL-1β and TNF-α in the present co culture model (FIG. 6), indicating polyclonally activated T cells as a prominent source for these cytokines.

Thus, the proinflammatory mature DC may produce at least 2 000 pg TNF-α/mL/$10^6$ cells, such as 32 000 pg/mL/$10^6$ cells and at least 500 pg IL-1β/mL/$10^6$ cells, such as 2 500 pg/mL/$10^6$ cells, during 24 h after withdrawal of stimuli.

Similar to the production of IL-1β and TNF-α, the IFN-γ production was shown to be produced most abundantly when using mature DCs that had been coated with SEB in the co cultures (FIG. 7), most likely due to the polyclonal activation of T cells. The addition of PBMCs to TLR and IFN-γ stimulated DCs slightly induced the production of IFN-γ, possibly secreted by NK cells activated by IL-12 produced by the proinflammatory mature DC 104.

Figure 5A:
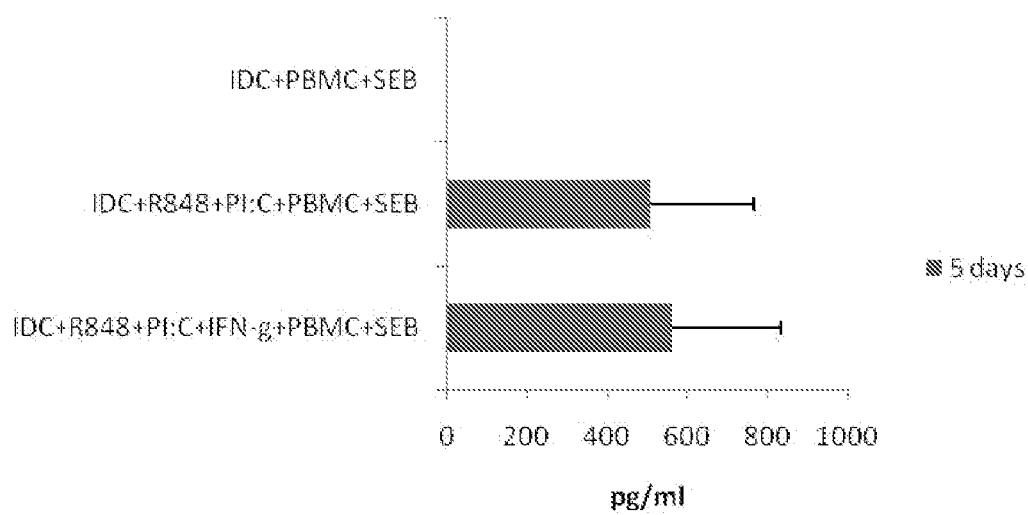
FIG. 5 are graphs showing production of IL-1β and TNF-α by a composition according to the second aspect.
Figure 5B:
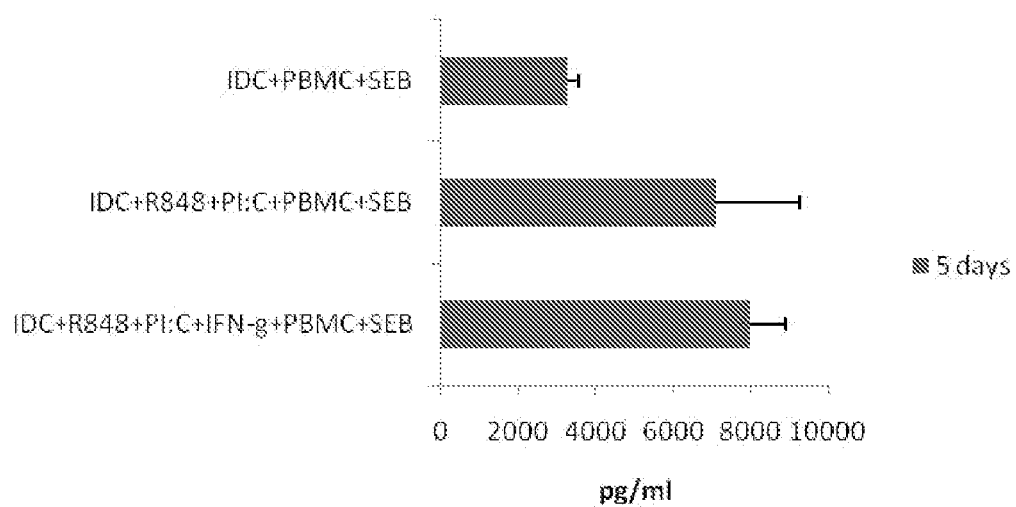
Figure 6A:
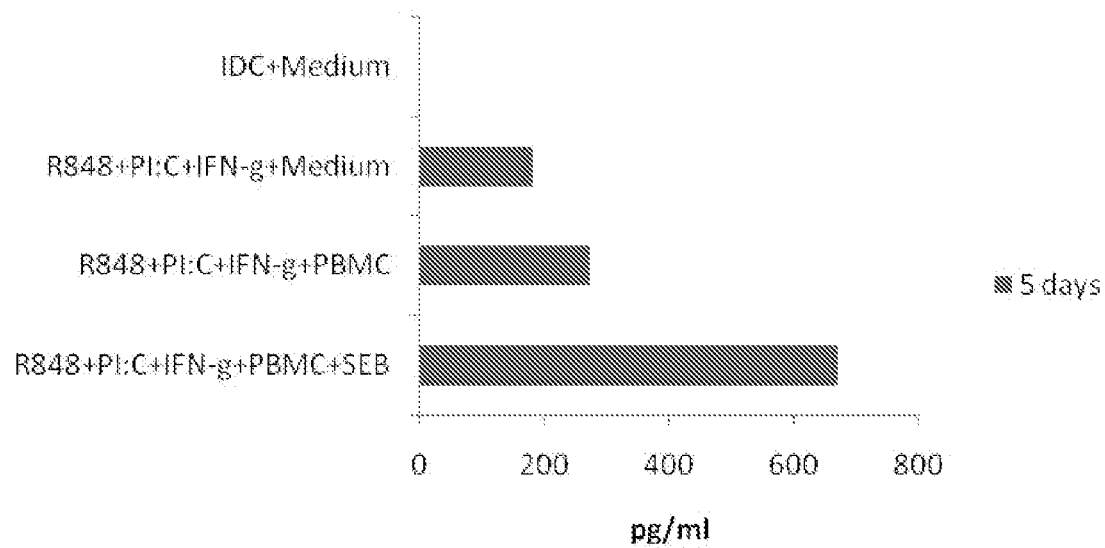
FIG. 6 are graphs showing production of IL-1β and TNF-α by a composition according to the second aspect.
Figure 6B:
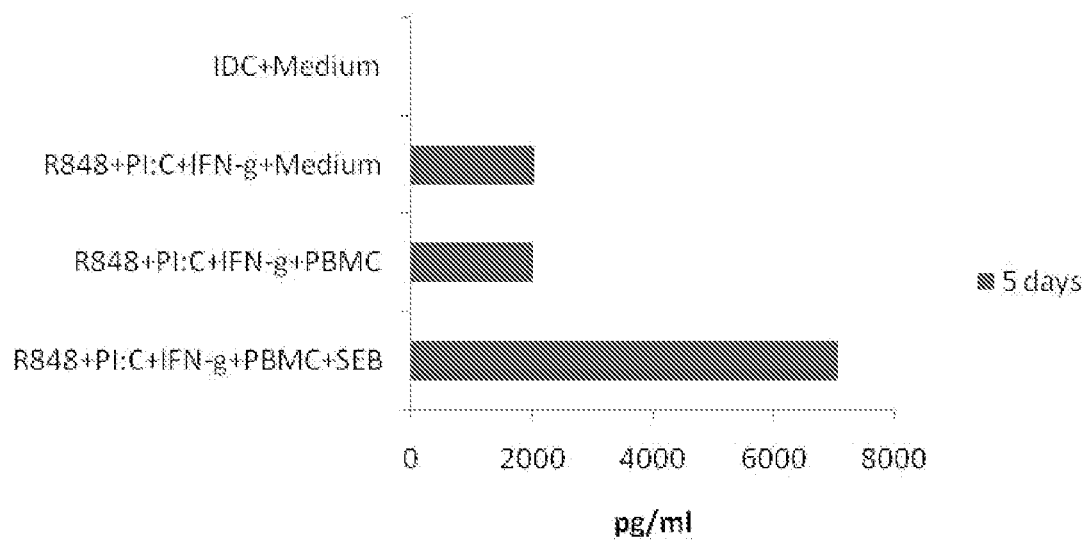

FIG. 5 shows cytokine levels of IL-1β (FIG. 5A) and TNF-α (FIG. 5B) as measured by ELISA. FIG. 6 shows cytokine levels of IL-1β (FIG. 6A) and TNF-α (FIG. 6B) as measured by ELISA, but with addition of medium, PBMC or PBMC/SEB. The data shown in FIG. 5 is mean values±SD from four individual and FIG. 6 show results from one experiment.

Figure 7:
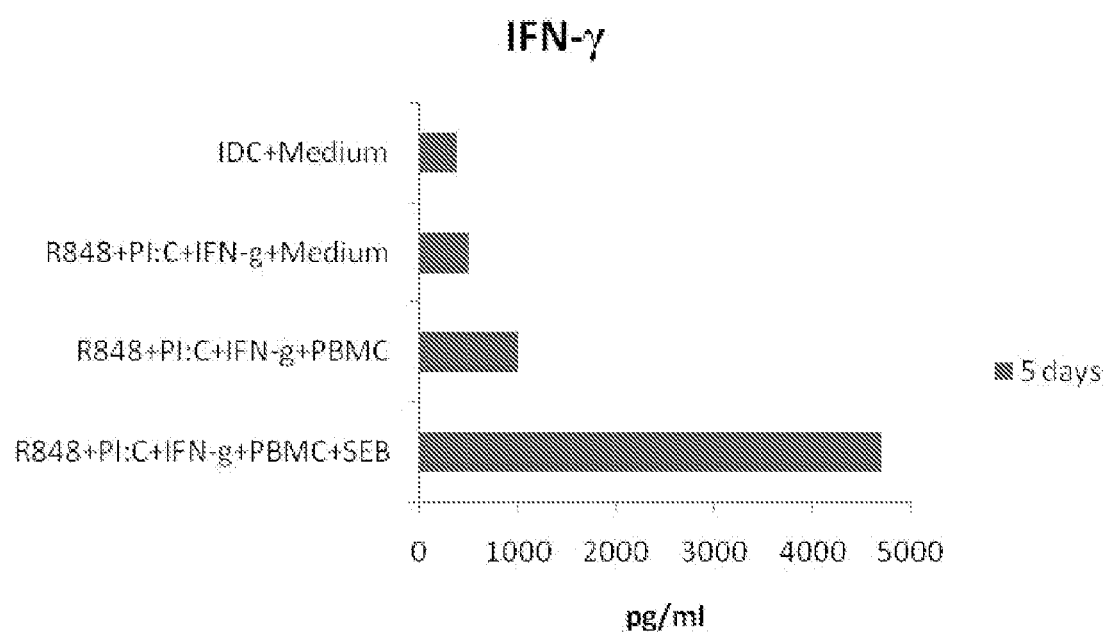
FIG. 7 is a graph showing production of IFN-γ by a composition according to the second aspect.

FIG. 7 shows cytokine levels of IFN-γ in supernatants as measured by ELISA. The data shown in FIG. 7 is from one experiment.

The respective X-axis in FIGS. 5, 6 and 7 shows the amount of the respective substance produced in pg/mL/2.5×10⁵ cells, during 24 h after withdrawal of stimuli. The respective Y-axis show the different combinations measured.

Phenotypical Maturation of Bystander Immature DCs

Figure 8A:
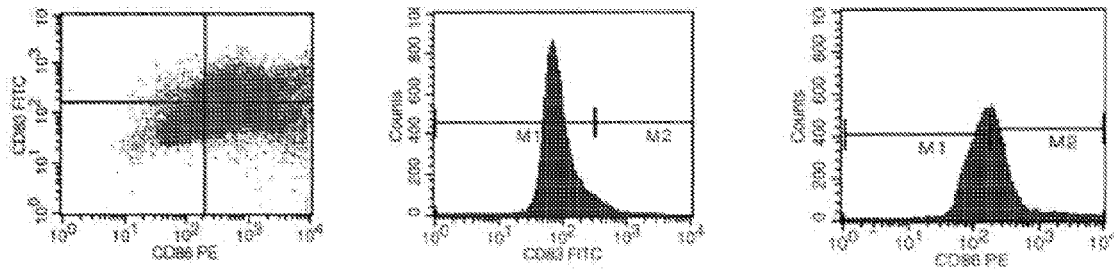
FIG. 8 are FACS graphs showing the influence of different substances on maturation of iDCs.
Figure 8B:
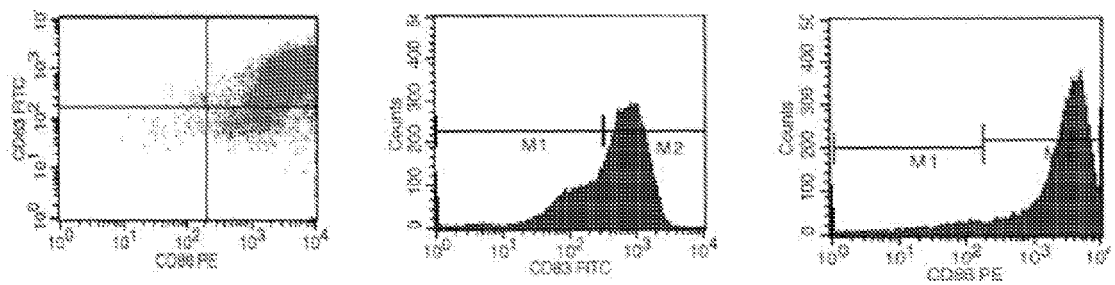
Figure 8C:
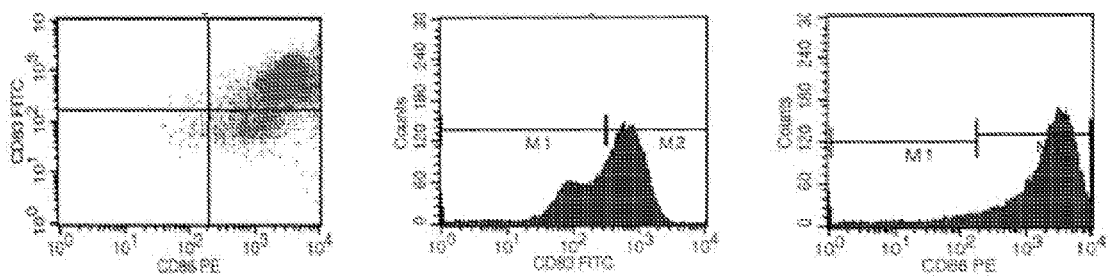

Supernatants from co cultures of non-coated or SEB-coated proinflammatory mature DC 104 and allogeneic PBMCs 101 were subsequently investigated as to ability to induce a phenotypical maturation of bystander immature DCs. Thus, a composition 100 comprising proinflammatory mature DC 104 according to any of the preceding claims and peripheral blood mononuclear cells (PBMCs) 101 is provided. Supernatants from these cell co cultures were used to stimulate immature bystander DCs obtained from adherent monocytes cultured for 5 days in GM-CSF and IL-4. After 24 h of stimulation, the cells were harvested for FACS analysis. Anti-human CD86 and CD83 were used to examine the expression of co-stimulatory molecules (CD86) and maturation markers (CD83), respectively. Supernatants from co cultures of proinflammatory mature DC 104 that had been matured with combined TLR stimulation, i.e. by adding poly-I:C, R848 to the iDCs 103, followed by SEB-coating induced a prominent expression of CD86 and CD83 of bystander DCs, as shown in FIG. 8. Thus, the composition 100 may comprise a superantigen. Addition of IFN-γ during TLR mediated maturation of vaccine DCs did not contribute to any additional, supernatant-induced, phenotypic maturation of bystander immature DCs, as seen in FIG. 8C.

FIG. 8 shows the influence of SEB and TLR ligands, i.e. inducers of maturation, on immature DCs 103. Adherent monocytes were incubated in GM-CSF and IL-4 for 5 days to obtain iDCs 103. Supernatants from a MLR with SEB/TLR stimulated proinflammatory mature DC 104 and PBMCs 101 were added day 5 followed by another incubation for 24 h. In order to study the costimulatory molecules and maturation markers, the cells were harvested and stained with anti-human CD86 and CD83. Maturation and co-stimulatory surface markers were highly induced by TLR ligands and SEB. Results shown are from one representative experiment out of two.

Figure 9A:
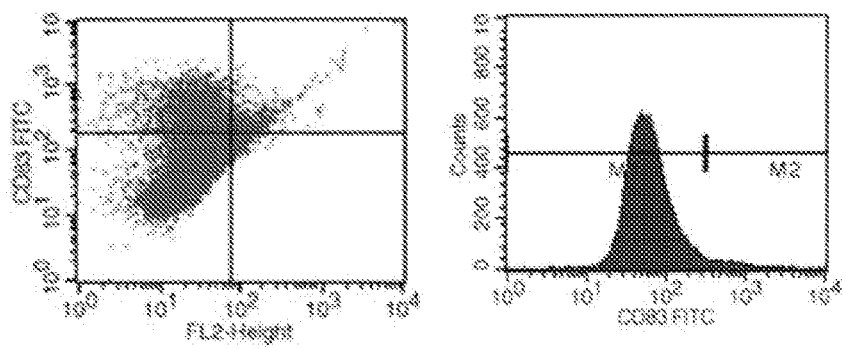
FIG. 9 are FACS graphs showing the influence of proinflammatory mature DC according to the first aspect, or a composition according to the second aspect, on maturation of iDCs.
Figure 9B:
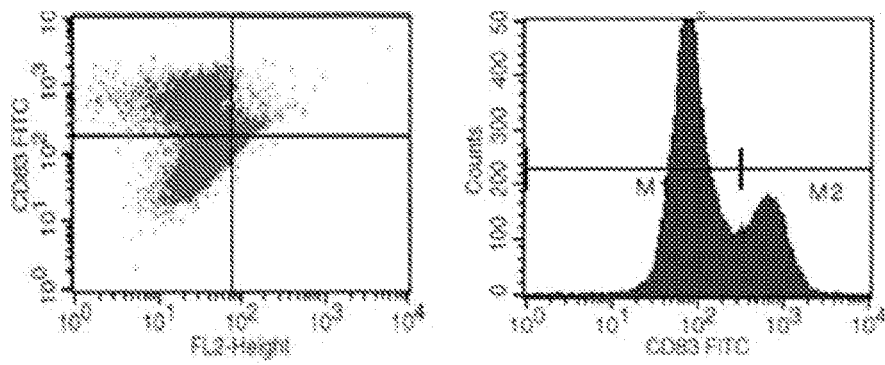
Figure 9C:
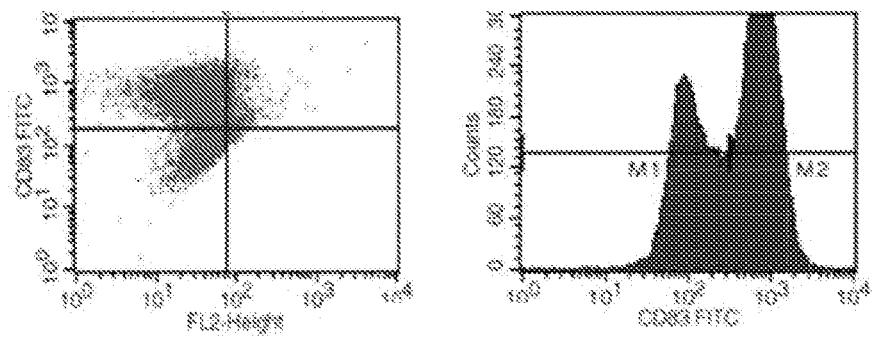
Figure 9D:
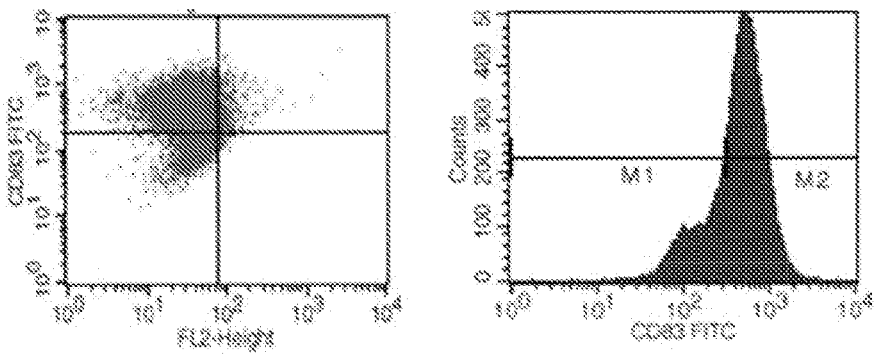

Supernatants from cell cultures only containing proinflammatory mature DC 104 that have been matured with combined TLR stimulation plus IFN-γ induced a substantial expression of CD83 on bystander DCs, as seen in FIG. 9B. As seen in FIG. 9C, CD83-expression was further enhanced by supernatants from co cultures with allogeneic PBMCs and proinflammatory mature DC 104. Finally, supernatants from co cultures with SEB-coated proinflammatory mature DC 104 and allogeneic PBMCs 101 induced the strongest expression of CD83, as seen in FIG. 9D, indicating that inclusion of SEB in proinflammatory mature DC 104-allogeneic PBMC 101-co cultures 100 is important to induce maximal supernatant-induced maturation of immature bystander DCs.

In view of the abovementioned results, according to an aspect, a proinflammatory mature DC 104, or a composition 100, for use as a medicament is provided.

According to an aspect, a proinflammatory mature DC 104, or a composition 100, for use in treatment of cancer is provided.

According to an aspect, use of proinflammatory mature DC 104, or a composition 100 for the manufacture of a medicament for treatment of cancer is provided.

The proinflammatory mature DC 104, or a composition 100 may be injected intratumorally.

In an embodiment, the cancer is chosen from the group consisting of: breast cancer, prostate cancer renal cancer, intestinal cancer, malignant gliomas, osteosarcoma, malignant melanoma, pancreatic cancer, malignant lymphomas and eosophagal cancer.

According to an aspect, a proinflammatory mature DC 104 or a composition 100, for use as a medicament in an individual other than the source of, such as a donor, the proinflammatory mature DC 104 or the PBMCs 101 is provided.

According to an aspect, a proinflammatory mature DC 104, or a composition 100, for use in treatment of cancer in an individual other than the source of, such as a donor, the proinflammatory mature DC 104 or the PBMCs 101 is provided.

Intratumoral Injection

As stated above, the proinflammatory mature DC 104, or a composition 100 may be injected intratumorally to produce an inhibitory effect on tumor growth.

To show this, a rat study was performed by Visionar Preclinical AB in Uppsala, Sweden, according to the following description.

Fifteen female Fischer rats were used in this study. After acclimatization (minimum one week), a 100 µl cell suspension comprising 10⁶ MAT B III cells (originally isolated from rat mammary gland adenocarcinoma) in RPMI medium was injected subcutaneously at the left rear flank of the animals (Day −4). Four days later a second tumor was induced on the right rear flank (Day 0). The proinflammatory mature DC 104 (produced as described above) or vehicle alone (PBS buffer with 10% (volume) fetal calf serum (FCS)) was injected into the first (left rear flank) tumor four days after the installation of the second (right rear flank) tumor (Day 4). The dosage of proinflammatory mature DC 104 was 20 µl per animal, comprising 10⁵ proinflammatory mature DC 104 cells. The growth of first and second tumor was recorded throughout the study. The animal experimental part of the study was approved by the regional animal experimental ethics committee in Uppsala, Sweden (C320/9).

An overview of the experimental design is seen in Table 1 below.

TABLE 1

Experimental design. The first column is the group, followed by number of participating rats (N), unique ID of participating rats, specification of induction of Tumor 1 and 2, and finally treatment specification, respectively.

| Group | N | ID | Tumor 1 | Tumor 2 | Treatment |
|---|---|---|---|---|---|
| Control | 6 | 658, 659, 662, 667, 668, 671 | $1 \times 10^6$ cells left side (Day −4) | $1 \times 10^6$ cells right side (Day 0) | Vehicle intra-tumorally LEFT (Day 4) |
| Proinflammatory mature DC 104 | 9 | 657, 660, 661, 663, 664, 665, 666, 669, 670 | $1 \times 10^6$ cells left side (Day −4) | $1 \times 10^6$ cells right side (Day 0) | $0.1 \times 10^6$ DC cells 104 intra-tumorally LEFT (Day 4) |

On the day of intratumoral vaccination in the first, left rear flank, tumor (Day 4), the animals were randomized into the two different groups based on the volume of the left tumor. In both the control and the proinflammatory mature DC 104 group, the intra-tumoral injections were done with a vehicle of PBS buffer with 10% (volume) fetal calf serum.

Every second day animals were checked for tumor growth. When palpable, the size of the tumors was measured with use of a calliper. The length and width of the tumor was recorded. The tumor volume was calculated by the formula: length (cm)×width (cm)×width (cm)×0.44.

The original plan was to euthanize three animals from the proinflammatory mature DC 104 group at Day 7 and all other animals at Day 15 (eleven days after injection of the second tumor). However, at Day 7 the left tumors in one control animal and in seven animals in the proinflammatory mature DC 104 group (given vehicle or vehicle+vaccine cells, respectively) were larger than 2 $cm^3$ and these eight animals were therefore euthanized. Two days later (Day 9), the left (first) tumor in the remaining seven animal had also grown past the ethical limit and the animals were thus euthanized.

The tumors were dissected, weighed, and frozen in dry ice and stored at −70° C. for subsequent histopathology.

The frozen tumors (both left and right) sent to MicroMorph for histopathological analysis are seen in Table 2 below. Eight μm cryosections were prepared and stained with hematoxylin/eosin and for DCs/macrophages (mouse anti rat CD68), NK cells (mouse anti rat CD161a), and CD8 positive cells (CD8+ T cells and also CD8+ DCs/macrophages), according to methods well known to a person skilled in the art.

The number of immunogenic cells in the different tumors was scored blindly as follows: few positive cells (1+), moderate number of positive cells (2+) or high numbers of positive cells (3+).

TABLE 2

Frozen tumors sent for histopathological analysis. Columns show Rat ID, Group and Experimental day of euthanization, respectively

| ID | Group | Experimental day |
|---|---|---|
| 659 | Control | 7 |
| 661 | Proinflammatory mature DC 104 | 7 |
| 662 | Control | 9 |
| 664 | Proinflammatory mature DC 104 | 9 |
| 665 | Proinflammatory mature DC 104 | 7 |
| 667 | Control | 9 |
| 670 | Proinflammatory mature DC 104 | 9 |

Analysis of results from the different groups regarding tumor volumes were performed using t-test and repeated measures ANOVA (PASW v 18 on a HP Compac dc 7700p computer). Descriptive statistics of tumor volume are presented in Tables 3 and 4 below.

TABLE 3

Tumor volume (TV) different days (d*). The table shows the mean tumor volume (mL), standard error of mean (SEM), and number of animals (N) throughout the study.

| | Vehicle control Tumor | | | | | | Proinflammatory mature DC 104 Tumor | | | | | |
|---|---|---|---|---|---|---|---|---|---|---|---|---|
| | First tumor | | | Second tumor | | | First tumor | | | Second tumor | | |
| | Mean | SEM | Valid N | Mean | SEM | Valid N | Mean | SEM | Valid N | Mean | SEM | Valid N |
| TV d2 | 0.03 | 0.02 | 6 | — | — | 0 | 0.04 | 0.02 | 9 | — | — | 0 |
| TV d4 | 0.20 | 0.05 | 6 | — | — | 0 | 0.20 | 0.06 | 9 | — | — | 0 |
| TV d6 | 1.17 | 0.16 | 6 | 0.04 | 0.02 | 6 | 1.40 | 0.22 | 9 | 0.01 | 0.01 | 9 |
| TV d7 | 2.02 | 0.61 | 6 | 0.09 | 0.04 | 6 | 3.35 | 0.55 | 9 | 0.05 | 0.02 | 9 |
| TV d9 | 4.43 | 0.25 | 5 | 0.68 | 0.08 | 5 | 4.32 | 1.04 | 2 | 0.36 | 0.04 | 2 |

A repeated measurement ANOVA was used to analyse tumor volumes from Day 6 to Day 9. The first and second tumor was analysed separately. Due to handling of missing values in the repeated measurements analysis, the last measured value was carried forward.

TABLE 4

The mean tumor volume (mL), standard error of mean (SEM), and number of animals (N) with the last measured value carried forward.

| | Vehicle control Tumor | | | | | | Proinflammatory mature DC 104 Tumor | | | | | |
|---|---|---|---|---|---|---|---|---|---|---|---|---|
| | First tumor | | | Second tumor | | | First tumor | | | Second tumor # | | |
| | Mean | SEM | Valid N | Mean | SEM | Valid N | Mean | SEM | Valid N | Mean | SEM | Valid N |
| TV d6 | 1.17 | 0.16 | 6 | 0.04 | 0.02 | 6 | 1.40 | 0.22 | 9 | 0.01 | 0.01 | 9 |
| TV d7 | 2.02 | 0.61 | 6 | 0.09 | 0.04 | 6 | 3.35* | 0.55 | 9 | 0.05 | 0.02 | 9 |
| TV d9 | 4.53* | 0.22 | 6 | 0.57* | 0.13 | 6 | 3.96* | 0.48 | 9 | 0.12‡ | 0.05 | 9 |

*P < 0.05 compared with day 6 within the group.
# P < 0.05 compared over all with the corresponding tumor in the control group.
‡P < 0.05 compared with the corresponding tumor in the control group.

Descriptive statistics of tumor weight are presented in Table 5 below.

TABLE 5

Mean tumor weight (TW, g), standard error of mean (SEM), and number of animals (N) at the different days of euthanasia.

| | Vehicle control Tumor | | | | | | COMBIG-DC Tumor | | | | | |
|---|---|---|---|---|---|---|---|---|---|---|---|---|
| | First tumor | | | Second tumor | | | First tumor | | | Second tumor | | |
| | Mean | SEM | Valid N | Mean | SEM | Valid N | Mean | SEM | Valid N | Mean | SEM | Valid N |
| TW d7 | 3.3491 | — | 1 | 0.1992 | — | 1 | 3.1209 | 0.3819 | 7 | 0.1423 | 0.0292 | 7 |
| TW d9 | 4.0094 | 0.3604 | 5 | 0.6090 | 0.0690 | 5 | 4.0201 | 0.3530 | 2 | 0.2740* | 0.0104 | 2 |

*$P < 0.05$ compared with the corresponding tumor in the control group (t-test).

Figure 10:
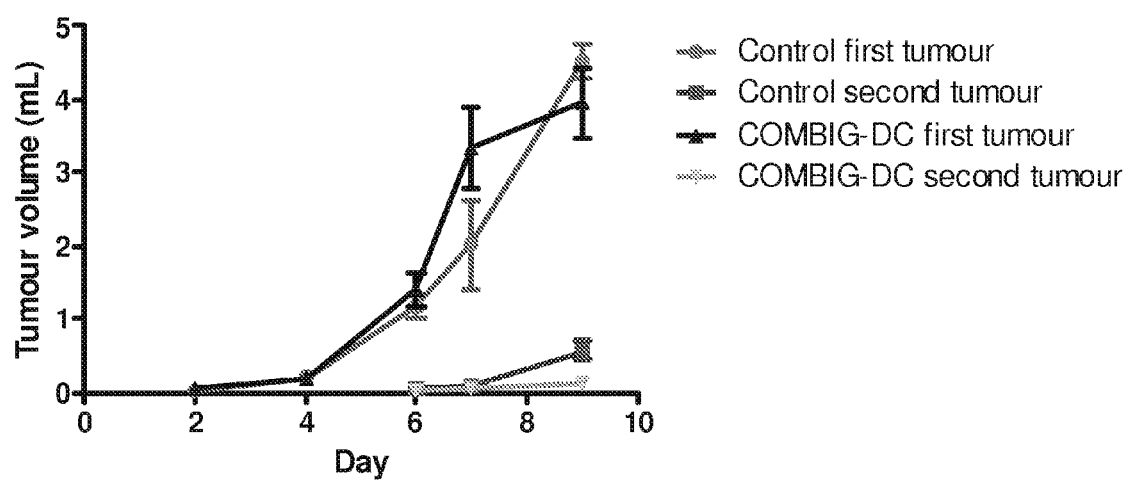
FIG. 10 is a graph showing tumor volume in a study regarding an embodiment.

FIG. 10 is a graph showing tumor volume (mL) of the different tumors in the different groups (COMBIG-DC denotes proinflammatory mature DC 104). When animals were removed from the study the last measured value was carried forward. Values are mean±SEM. It can clearly be seen that rats treated with proinflammatory mature DC 104 had smaller tumor volume, both regarding first and second tumor.

The first tumor grew very fast and all animals had to be euthanized earlier than planned due to the large tumor volume. Seven out of nine animals in the proinflammatory mature DC 104 group and one out of six animals in the control group had to be euthanized at day 7 and the remaining animals at day 9. To be able to perform statistical analysis on the material, the last measured tumor volume from day 7 was carried forward to day 9. This could possibly render a falsely lower volume of the first (vaccine-injected) tumor at day 9 and the fact that more animals were removed from the proinflammatory mature DC 104 group should be considered when analysing the results on volume and weight of the first (left) tumor. A repeated measurement ANOVA was then used to analyse tumor volumes from Day 6 to Day 9. The first and second tumor was analyzed separately.

The larger tumor volumes of the first tumor in the proinflammatory mature DC 104 group at day 7 could be explained by an ongoing inflammatory response to the injected dendritic cells since immunohistochemistry revealed increased numbers of infiltrating inflammatory cells in these first tumors in the proinflammatory mature DC 104 group compared to the control group (se below).

The second tumor in the proinflammatory mature DC 104 group had a statistically significant reduction in tumor volume compared to the control group. Furthermore, a statistically significant lower weight of the two second tumors that were removed at day 9 in the proinflammatory mature DC 104 group was found compared with the control group.

The tumors were frozen and cryosections were prepared and stained with hematoxylin/eosin and for DCs/macrophages (mouse anti rat CD68), NK cells (mouse anti rat CD161a), and CD8 positive cells (CD8+ T cells and also CD8+ DCs/macrophages). The tumors were composed of malignant tumor cells surrounded by a loose connective capsule of variable thickness. Strands of connective fibres were found intermingling with the tumor cells. Areas of necrotic tumor cells were seen in all samples. Pools of crystallized material were seen in some of the first tumors (injected). Since this was only found in the first tumors it is most likely a reminiscent of the injected material.

A summary of this is presented in Table 6 below.

TABLE 6

The results of the histopathological analysis at the different day of euthanasia (Exp. day). The values are scores of number of DCs/macrophages (CD68), NK-cells (CD161a), DCs/macrophages (CD8a) and cytotoxic T cells (CD8a). Morphological evaluation of the tumors was done on sections with H/E staining.

| ID | Group | Exp. day | Tumor | CD68 | CD161a | CD8a | H/E |
|---|---|---|---|---|---|---|---|
| 659 | Control | 7 | First | 1-2+ | 1-2+ | 1-2+ | Approx. half of the tumor necrotic |
| | | | Second | 3+ | 2+ | 2-3+ | Approx. half of the tumor necrotic |
| 661 | Proinflammatory mature DC 104 | 7 | First | 3+ | 2+ | 3+ | Approx. half of the tumor necrotic |
| | | | Second | 3+ | 2+ | 3+ | Approx. half of the tumor necrotic |
| 662 | Control | 9 | First | 2+ | 1+ | 2+ | Approx. half of the tumor necrotic |
| | | | Second | 2+ | 1+ | 2+ | Mostly viable tumor cells |
| 664 | Proinflammatory mature DC 104 | 9 | First | 1-2+ | 1+ | 2+ | Mostly viable tumor cells |
| | | | Second | 2+ | 1+ | 2+ | Mostly viable tumor cells |
| 665 | Proinflammatory mature DC 104 | 7 | First | 3+ | 2+ | 3+ | Mostly necrotic tumor cells |
| | | | Second | 3+ | 1-2+ | 2-3+ | Mostly viable tumor cells |
| 667 | Control | 9 | First | 2+ | 1+ | 2+ | Approx. half of the tumor necrotic |
| | | | Second | 2+ | 1+ | 2+ | Mostly viable tumor cells |
| 670 | Proinflammatory mature DC 104 | 9 | First | 2-3+ | 1+ | 2-3+ | Mostly necrotic tumor cells |
| | | | Second | 3+ | 1-2+ | 2-3+ | Mostly viable tumor cells |

Tumor infiltrating CD8a, CD68 and CD161a positive cells were found in all analyzed samples. Positive cells were seen both in the capsule surrounding the tumor as well as in tumor cell areas. Although the result were not conclusive there seemed to be a tendency that animals treated with proinflammatory mature DC 104 had a higher presence of the investigated cells.

Thus, there was a tendency that the treatment with intratumoral injection of proinflammatory mature DC 104 induced an increased recruitment of DCs/macrophages, NK cells and cytotoxic T-cells to the tumors with a following reduction in volume and weight of the second tumor.

Figure 11:
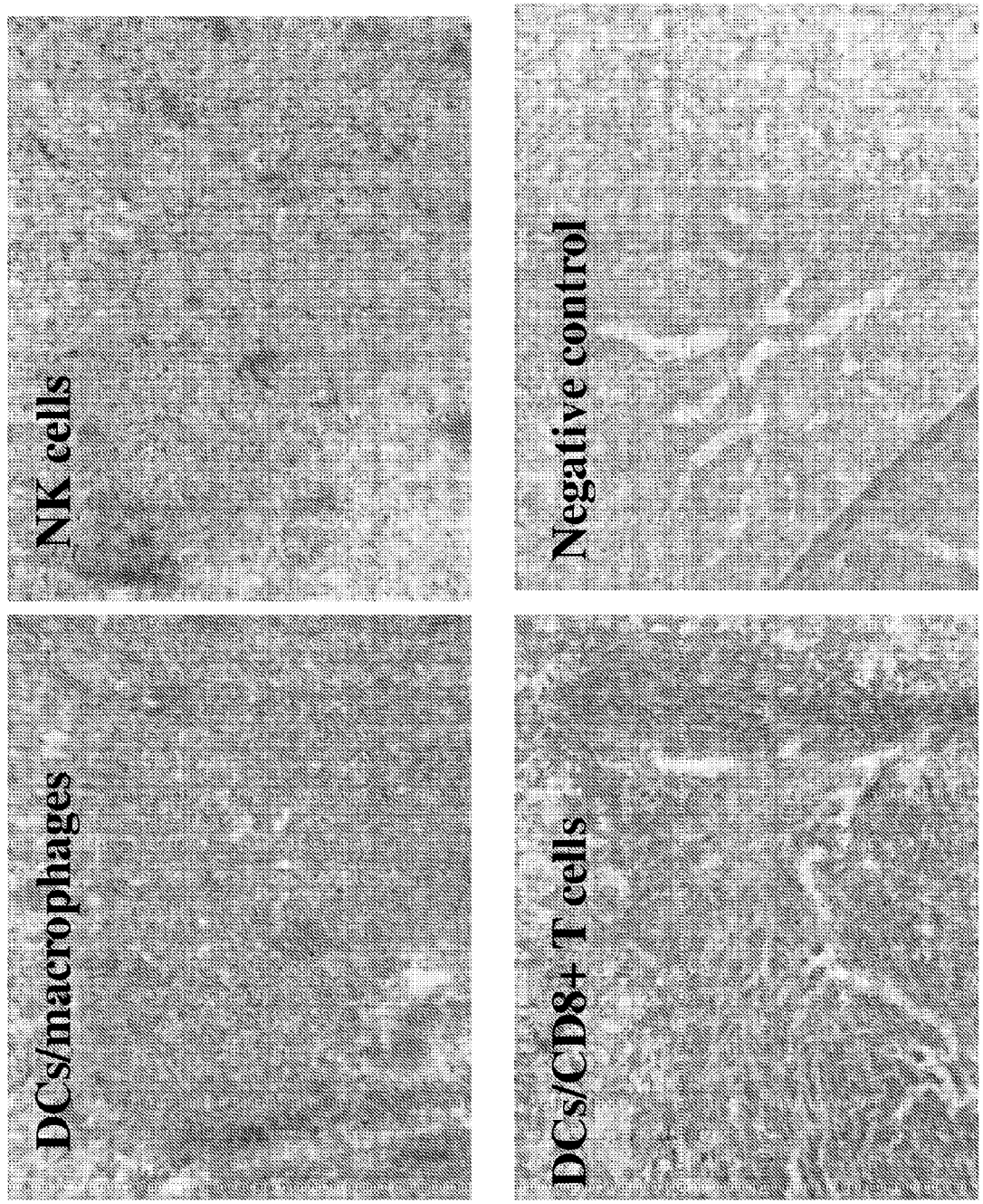
FIG. 11 shows pictures of the histopathological results (primary tumor) study regarding an embodiment.

FIG. 11 shows pictures of the histopathological results for macrophages, NK-cells, cytotoxic T-cells (DCs/CD8+) 3 days after intratumoral injection of proinflammatory mature DC 104 in primary tumor.

Figure 12:
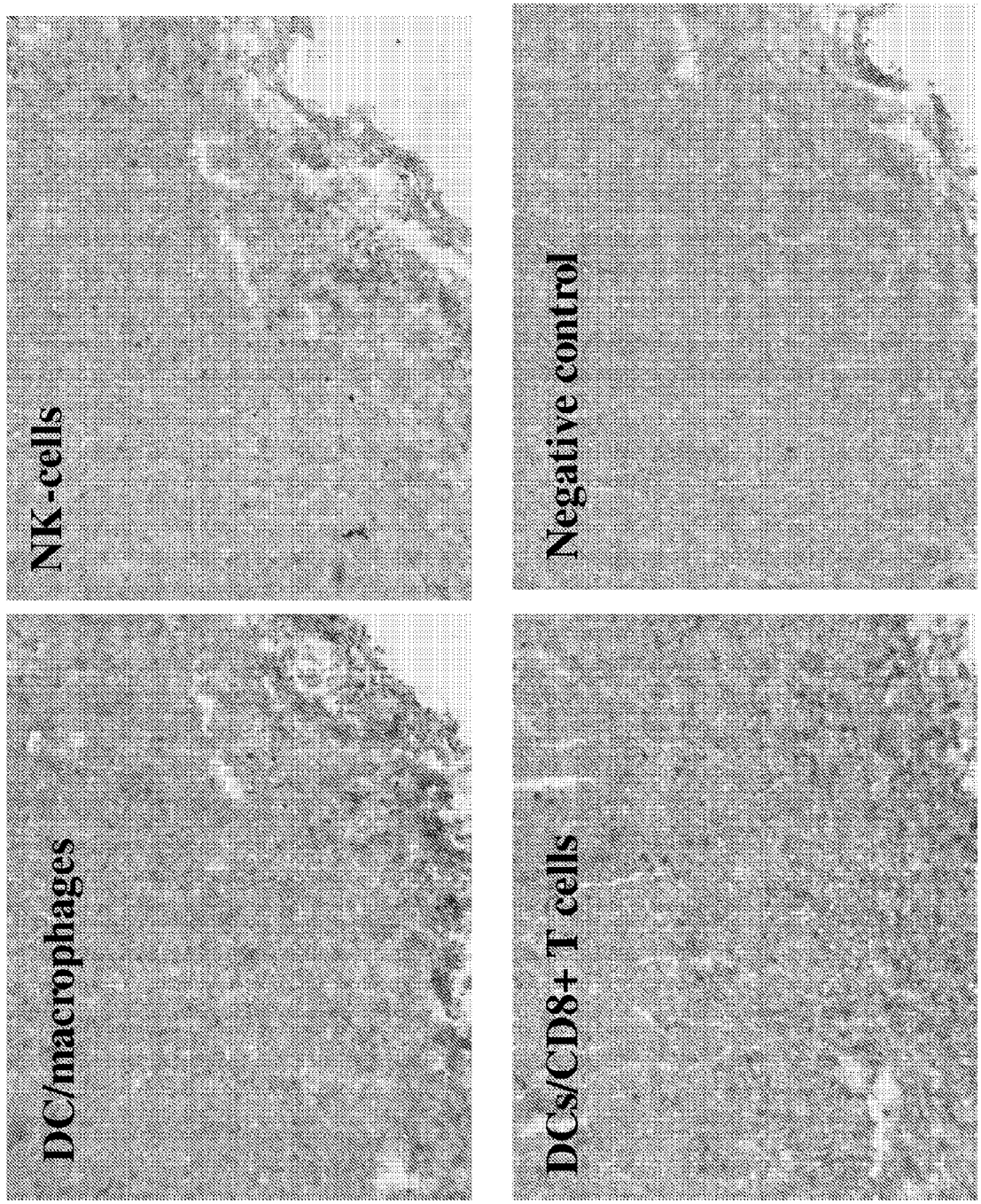
FIG. 12 shows pictures of the histopathological control results (primary tumor) in a study regarding an embodiment.

FIG. 12 shows pictures of the histopathological results of the corresponding control, with intratumoral injection of vehicle only.

Figure 13:
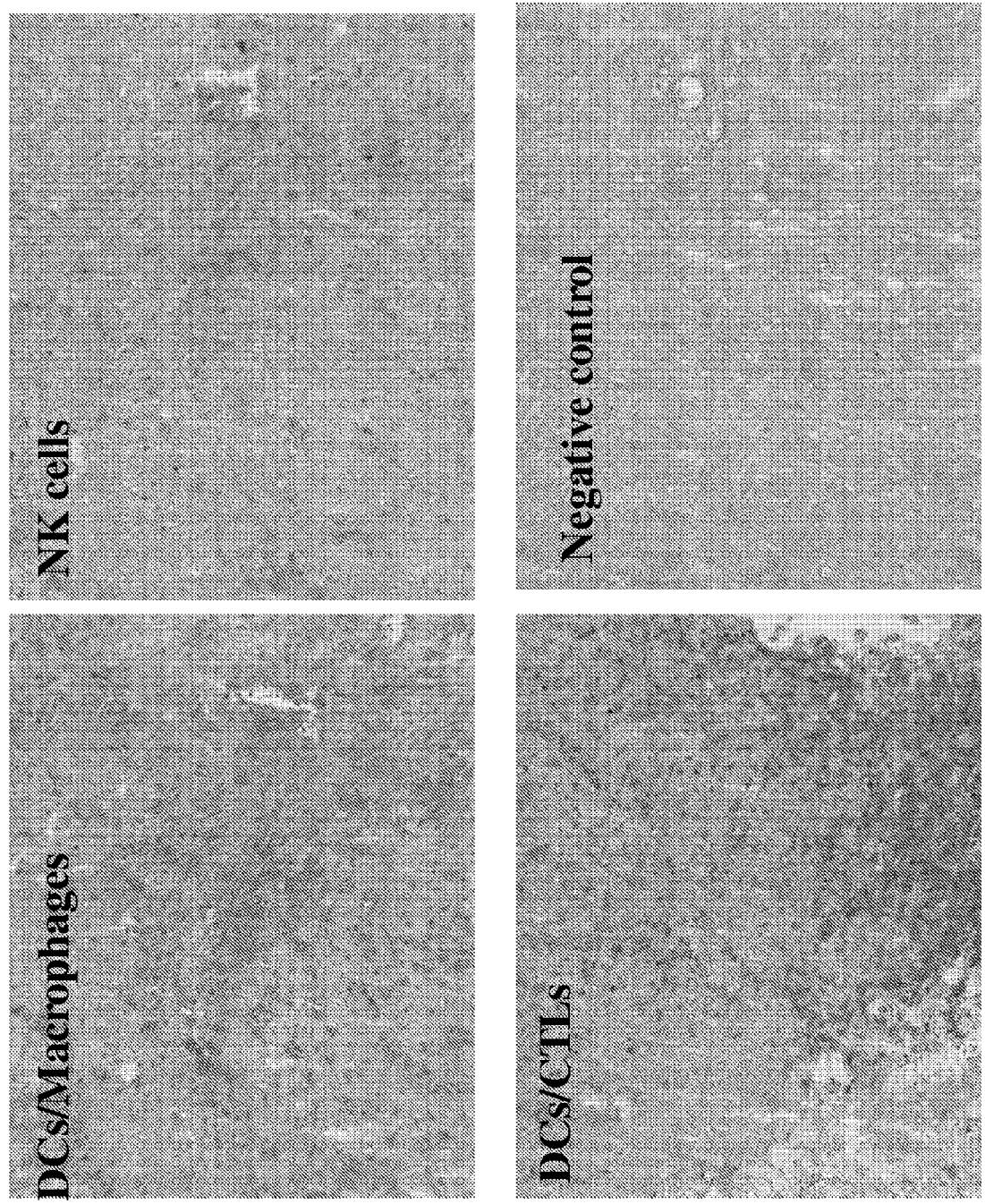
FIG. 13 shows pictures of the histopathological results (secondary tumor) in a study regarding an embodiment.

Thus it can be seen that DCs/macrophages, NK-cells and cytotoxic T-cells were recruited to the tumor after injection with proinflammatory mature DC 104, but not after injection with vehicle only. FIG. 13 shows pictures of the histopathological results for DCs/macrophages, NK-cells and cytotoxic T-cells of secondary tumors 5 days after intratumoral injection of proinflammatory mature DC 104 in primary tumor.

Figure 14:
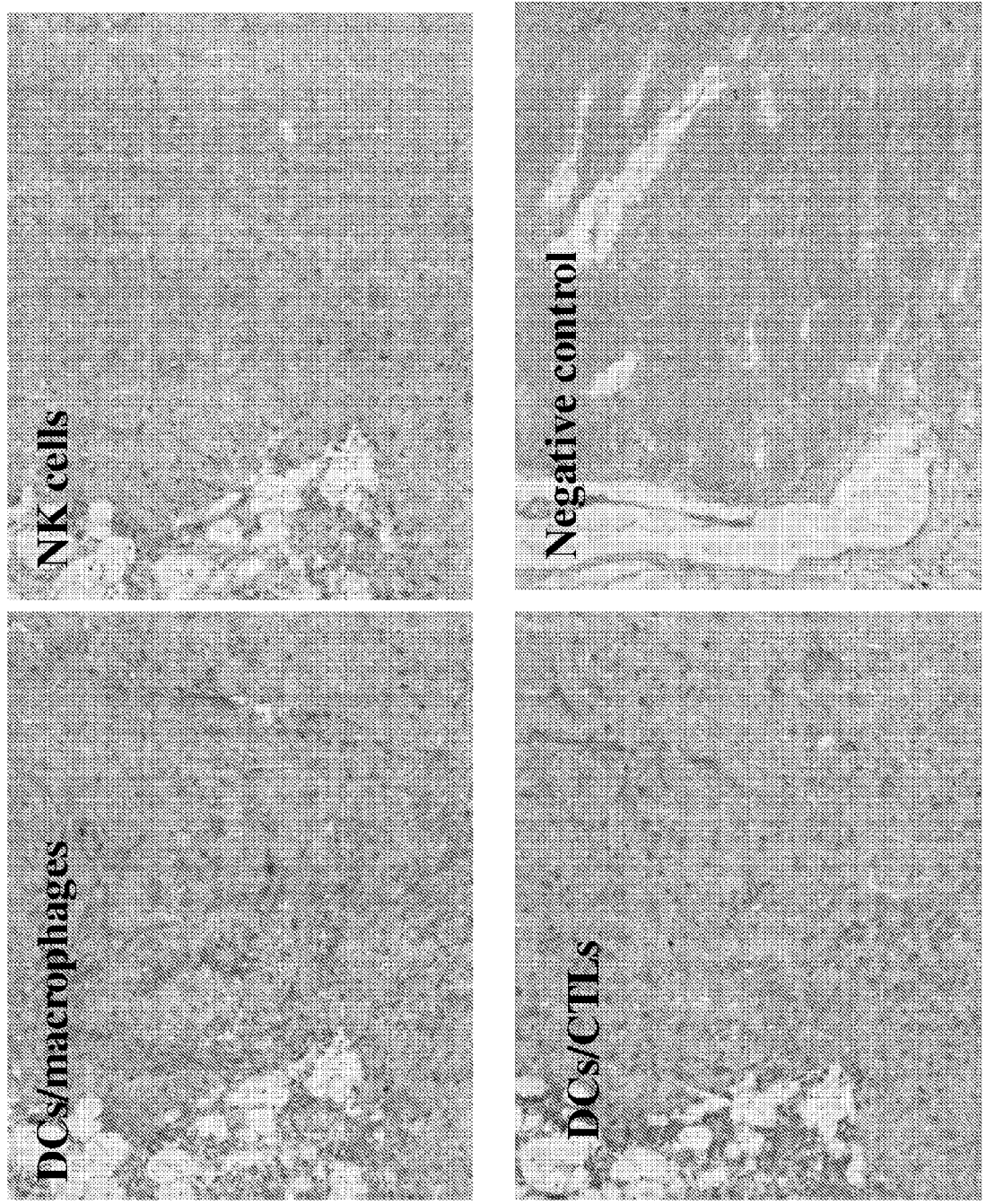
FIG. 14 shows pictures of the histopathological control results (secondary tumor) in a study regarding an embodiment.

FIG. 14 shows pictures of the histopathological results of the corresponding control, with intratumoral injection of vehicle only.

Thus it can be seen that DCs/macrophages, NK-cells and cytotoxic T-cells were recruited even to the secondary tumor (metastasis) after injection with proinflammatory mature DC 104 in the primary tumor, but in a lower degree after injection with vehicle only.

Taken together, this vaccine study in a tumor model indicate that intratumoral injection of proinflammatory mature DC 104 induce a prominent recruitment of inflammatory cells, including DCs, NK cells and T cells to the injection site (first tumor). Such intense recruitment of inflammatory cells probably explains the observed increase in tumor volume the first 2-3 days after injection. Intratumoral injection of proinflammatory mature DC 104 further induce a reduction of a distant tumor (right rumor), indicating a systemic anti-tumor effect.

In an embodiment, the cancer is chosen from the group consisting of: breast cancer, prostate cancer renal cancer, intestinal cancer, malignant gliomas, osteosarcoma, malignant melanoma, pancreatic cancer, malignant lymphomas and eosophagal cancer.

In an embodiment, the proinflammatory mature DC 104, or a composition 100 according to above, further comprise a pharmaceutically acceptable excipients, such as carriers, preservatives, adjuvants etc.

In an embodiment the excipient is 2% human serumalbumin, provided in physiological NaCl solution.

In an embodiment, both the mature DCs 104 and peripheral blood mononuclear cells (PBMCs) 101 are allogeneic in relation to the subject, i.e. originates from a donor which is MHC incompatible to the subject, such as fully MHC incompatible.

This has the advantage that the therapeutic composition can be pre-produced and stored, such as in a frozen state, prior to use. The allogenic nature of the composition in relation to the patient will also cause the composition to be more effective, as discussed above.

In an aspect, a method of treating a mammalian patient having a tumor is provided. The method comprises administering to the patient, once or several times, a therapeutically effective amount of a proinflammatory mature DC 104, or a composition 100, wherein a donor, from which the proinflammatory mature DCs 104 and/or the PBMCs 101 are taken, is not the patient.

The administration may be intratumoral injection.

In the claims, the term "comprises/comprising" does not exclude the presence of other elements or steps. Furthermore, although individually listed, a plurality of elements or method steps may be implemented by e.g. a single step. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

The invention claimed is:

1. A method for treating cancer in a subject in need thereof, the method comprising:
   stimulating an immature dendritic cell (DC) to become a non-migratory, proinflammatory mature DC ex vivo by treatment with polyinosinic-polycytidylic acid sodium salt (poly-I:C), resiquimod (R848), and interferon gamma (IFN-γ), but not with prostaglandin E2 (PGE2); and
   injecting the non-migratory, proinflammatory mature DC into a tumor of the subject;
   wherein the immature DC is obtained from a person other than the subject in need thereof.

2. The method according to claim 1, wherein the immature DC is further stimulated with at least one substance selected from the group consisting of interferon α (IFN-α), interleukin 1 beta (IL-1β), and tumor necrosis factor α (TNF-α).

3. The method according to claim 1, wherein the non-migratory, proinflammatory mature DC produces at least 25 000 pg IL-12/mL/$10^6$ cells, at least 100 000 pg CXCL9/mL/$10^6$ cells, and at least 40 000 pg CCL3/mL/$10^6$ cells during 24 hours after withdrawal of stimuli.

4. The method according to claim 3, wherein the non-migratory, proinflammatory mature DC further produces at least 2 000 pg TNF-α/mL/$10^6$ cells and at least 500 pg IL-1β/mL/$10^6$ cells during 24 hours after withdrawal of stimuli.

5. The method according to claim 1, wherein the cancer is selected from the group consisting of breast cancer, prostate cancer, renal cancer, intestinal cancer, malignant glioma, osteosarcoma, malignant melanoma, pancreatic cancer, malignant lymphoma, and eosophagal cancer.

6. The method according to claim 1, wherein the non-migratory, proinflammatory mature DC is formulated into a pharmaceutical composition comprising a pharmaceutically acceptable excipient.

7. The method according to claim 6, wherein the composition further comprises a superantigen.

8. The method according to claim 6, wherein the pharmaceutical composition further comprises a peripheral blood mononuclear cell (PBMC).

9. The method according to claim 8, wherein the PBMC has been obtained from a person other than the subject in need thereof.

10. A method for treating cancer in a subject in need thereof, the method comprising:
    generating an immature DC from a monocyte isolated from a population of PBMCs;
    stimulating the immature DC to become a non-migratory, proinflammatory mature DC ex vivo by treatment with poly-I:C, R848, and IFN-γ, but not with PGE2; and
    injecting the non-migratory, proinflammatory mature DC into a tumor of the subject;
    wherein the population of PBMCs is obtained from a person other than the subject in need thereof 11. The method according to claim 10, wherein the immature DC is further stimulated with at least one substance selected from the group consisting of IFN-α, IL-1β, and TNF-α.

12. The method according to claim 10, wherein the non-migratory, proinflammatory mature DC produces at least 25 000 pg IL-12/mL/$10^6$ cells, at least 100 000 pg CXCL9/mL/$10^6$ cells, and at least 40 000 pg CCL3/mL/$10^6$ cells during 24 hours after withdrawal of stimuli.

13. The method according to claim 12, wherein the non-migratory, proinflammatory mature DC further produces at least 2 000 pg TNF-α/mL/$10^6$ cells and at least 500 pg IL-1β/mL/$10^6$ cells during 24 hours after withdrawal of stimuli.

14. The method according to claim 10, wherein the cancer is selected from the group consisting of breast cancer, prostate cancer, renal cancer, intestinal cancer, malignant glioma, osteosarcoma, malignant melanoma, pancreatic cancer, malignant lymphoma., and eosophagal cancer.

15. The method according to claim 10, wherein the non-migratory, proinflammatory mature DC is formulated into a pharmaceutical composition comprising a pharmaceutically acceptable excipient.

16. The method according to claim 15, wherein the composition further comprises a superantigen.

17. The method according to claim 15, wherein the pharmaceutical composition further comprises a PBMC.

18. The method according to 17, wherein the PBMC has been obtained from a person other than the subject in need thereof 19. The method according to claim 10, wherein the immature DC is generated by culturing the isolated monocyte in an aqueous media comprising IL-4 and granulocyte macrophage colony-stimulating factor (GM-CSF) for 2 to 7 days.

20. The method according to claim 19, wherein the immature DC is generated by culturing the isolated monocyte in in an aqueous media comprising IL-4 and GM-CSF for 5 days.

* * * * *